(12) United States Patent
Gysling

(10) Patent No.: US 7,096,719 B2
(45) Date of Patent: Aug. 29, 2006

(54) APPARATUS FOR MEASURING PARAMETERS OF A FLOWING MULTIPHASE MIXTURE

(75) Inventor: Daniel L. Gysling, Glastonbury, CT (US)

(73) Assignee: CiDRA Corporation, Wallingford, CT (US)

( * ) Notice: Subject to any disclaimer, the term of this patent is extended or adjusted under 35 U.S.C. 154(b) by 0 days.

(21) Appl. No.: 10/756,922

(22) Filed: Jan. 13, 2004

(65) Prior Publication Data

US 2004/0194539 A1 Oct. 7, 2004

Related U.S. Application Data

(60) Provisional application No. 60/447,498, filed on Feb. 14, 2003, provisional application No. 60/440,014, filed on Jan. 14, 2003, provisional application No. 60/439,717, filed on Jan. 13, 2003.

(51) Int. Cl.
*G01N 29/024* (2006.01)

(52) U.S. Cl. .................. 73/61.75; 73/61.49; 73/19.03; 73/24.03; 73/24.04; 73/64.53

(58) Field of Classification Search ............... 73/19.03, 73/19.01, 24.04, 24.05, 61.49, 61.75, 64.44, 73/597, 861.27, 861.28, 861.29, 861.31
See application file for complete search history.

(56) References Cited

U.S. PATENT DOCUMENTS

| | | | | |
|---|---|---|---|---|
| 3,715,709 A | * | 2/1973 | Zacharias et al. .............. 367/95 |
| 3,751,979 A | | 8/1973 | Ims .......................... 73/861.27 |
| 3,781,895 A | | 12/1973 | Monser ....................... 343/708 |
| 3,851,521 A | | 12/1974 | Ottenstein .................... 73/40.5 |
| 3,885,432 A | | 5/1975 | Herzl ....................... 73/861.22 |
| 3,952,578 A | | 4/1976 | Jacobs ........................ 73/64.1 |
| 4,032,259 A | * | 6/1977 | Brown ......................... 417/43 |
| 4,048,853 A | | 9/1977 | Smith et al. ............. 73/861.25 |
| 4,080,837 A | | 3/1978 | Alexander et al. ......... 73/61.45 |
| 4,248,085 A | | 2/1981 | Coulthard ................ 73/861.06 |
| 4,320,659 A | | 3/1982 | Lynnworth et al. ........... 73/589 |

(Continued)

FOREIGN PATENT DOCUMENTS

DE        4306119        9/1994

(Continued)

OTHER PUBLICATIONS

Richard L. Gibson Jr. and M. Nafi Toksoz "Viscous attenuation of acoustic waves in suspensions", Jan. 5, 1989 pp. 1925-1934.

(Continued)

*Primary Examiner*—Hezron Williams
*Assistant Examiner*—Paul M. West

(57) ABSTRACT

An apparatus 10 is provided that measures the speed of sound propagating in a multiphase mixture to determine parameters, such as mixture quality, particle size, vapor/mass ratio, liquid/vapor ratio, mass flow rate, enthalpy and volumetric flow rate of the flow in a pipe or unconfined space, for example, using acoustic and/or dynamic pressures. The apparatus includes a pair of ultrasonic transducers disposed axially along the pipe for measuring the transit time of an ultrasonic signal to propagate from one ultrasonic transducer to the other ultrasonic transducer. A signal process, responsive to said transit time signal, provides a signal representative of the speed of sound of the mixture. An SOS processing unit then provides an output signal indicative of at least one parameter of the mixture flowing through the pipe. The frequency of the ultrasonic signal is sufficiently low to minimize scatter from particle/liquid within the mixture. The frequency based sound speed is determined utilizing a dispersion model to determine the at least one parameter of the fluid flow and/or mixture.

27 Claims, 15 Drawing Sheets

U.S. PATENT DOCUMENTS

| | | | |
|---|---|---|---|
| 4,445,389 A | 5/1984 | Potzick et al. | 73/861.27 |
| 4,520,320 A | 5/1985 | Potzick et al. | 328/133 |
| 4,561,310 A | 12/1985 | Barnard et al. | 73/861.02 |
| 4,677,305 A | 6/1987 | Ellinger | 73/290 V |
| 4,717,159 A | 1/1988 | Alston et al. | 330/129 |
| 4,896,540 A | 1/1990 | Shakkottai et al. | 73/861.02 |
| 4,932,262 A | 6/1990 | Wlodarczyk | 250/227.3 |
| 5,040,415 A | 8/1991 | Barkhoudarian | 73/198 |
| 5,060,506 A * | 10/1991 | Douglas | 73/24.01 |
| 5,083,452 A | 1/1992 | Hope | 73/61 R |
| 5,218,197 A | 6/1993 | Carroll | 250/227.19 |
| 5,285,675 A | 2/1994 | Colgate et al. | 73/23.2 |
| 5,289,726 A | 3/1994 | Miau et al. | 73/861.22 |
| 5,359,897 A | 11/1994 | Hamstead et al. | 73/597 |
| 5,363,342 A | 11/1994 | Layton et al. | 367/149 |
| 5,367,911 A | 11/1994 | Jewell et al. | 73/861.08 |
| 5,398,542 A | 3/1995 | Vasbinder | 73/40.5 |
| 5,524,475 A | 6/1996 | Kolpak et al. | 73/19.03 |
| 5,526,844 A | 6/1996 | Kamen et al. | 137/614.11 |
| 5,591,922 A | 1/1997 | Segeral et al. | 73/861.04 |
| 5,625,140 A * | 4/1997 | Cadet et al. | 73/24.01 |
| 5,708,211 A | 1/1998 | Jepson et al. | 73/861.04 |
| 5,741,980 A | 4/1998 | Hill et al. | 73/861.04 |
| 5,770,805 A | 6/1998 | Castel | 73/861.04 |
| 5,770,806 A | 6/1998 | Hiismaki | 73/861.29 |
| 5,835,884 A | 11/1998 | Brown | 73/861.04 |
| 5,845,033 A | 12/1998 | Berthold et al. | 385/12 |
| 5,948,959 A | 9/1999 | Peloquin | 73/1.83 |
| 6,016,702 A | 1/2000 | Maron | 73/705 |
| 6,151,958 A | 11/2000 | Letton et al. | 73/61.79 |
| 6,202,494 B1 | 3/2001 | Riebel et al. | 73/861.29 |
| 6,233,374 B1 | 5/2001 | Ogle et al. | 385/13 |
| 6,345,539 B1 | 2/2002 | Rawes et al. | 73/861.27 |
| 6,349,599 B1 | 2/2002 | Lynnworth et al. | 73/644 |
| 6,354,147 B1 | 3/2002 | Gysling et al. | 73/61.79 |
| 6,378,357 B1 | 4/2002 | Han et al. | 73/54.41 |
| 6,412,353 B1 | 7/2002 | Kleven et al. | 73/861.22 |
| 6,435,030 B1 | 8/2002 | Gysling et al. | 73/587 |
| 6,442,996 B1 | 9/2002 | Thurston et al. | 73/24.01 |
| 6,443,226 B1 | 9/2002 | Diener et al. | 166/241.6 |
| 6,450,037 B1 | 9/2002 | McGuinn et al. | 73/705 |
| 6,463,813 B1 | 10/2002 | Gysling | 73/862.59 |
| 6,536,291 B1 | 3/2003 | Gysling et al. | 73/861.42 |
| 6,550,342 B1 | 4/2003 | Croteau et al. | 73/800 |
| 6,558,036 B1 | 5/2003 | Gysling et al. | 374/147 |
| 6,587,798 B1 | 7/2003 | Kersey et al. | 702/50 |
| 6,601,005 B1 | 7/2003 | Eryurek et al. | 702/104 |
| 6,601,458 B1 | 8/2003 | Gysling et al. | 73/861.04 |
| 6,609,069 B1 | 8/2003 | Gysling | 702/48 |
| 6,658,945 B1 | 12/2003 | Kleven | 73/861.22 |
| 6,672,163 B1 * | 1/2004 | Han et al. | 73/597 |
| 6,691,584 B1 | 2/2004 | Gysling et al. | 73/861.42 |
| 6,698,297 B1 | 3/2004 | Gysling | 73/861.63 |
| 6,732,575 B1 * | 5/2004 | Gysling et al. | 73/61.79 |
| 6,782,150 B1 | 8/2004 | Davis et al. | 385/12 |
| 6,813,962 B1 | 11/2004 | Gysling et al. | 73/861.26 |
| 6,837,098 B1 | 1/2005 | Gysling et al. | 73/61.79 |
| 6,837,332 B1 | 1/2005 | Rodney | 181/105 |
| 6,862,920 B1 | 3/2005 | Gysling et al. | 73/61.79 |
| 6,868,737 B1 | 3/2005 | Croteau et al. | 73/800 |
| 6,889,562 B1 | 5/2005 | Gysling et al. | 73/861.42 |
| 6,898,541 B1 | 5/2005 | Gysling et al. | 902/100 |
| 2001/0020603 A1 | 9/2001 | Moorehead et al. | 210/741 |
| 2002/0064331 A1 | 5/2002 | Davis et al. | 385/12 |
| 2002/0095263 A1 | 7/2002 | Gysling | 702/45 |
| 2002/0123852 A1 | 9/2002 | Gysling et al. | |
| 2002/0129662 A1 | 9/2002 | GYsling et al. | |
| 2003/0038231 A1 | 2/2003 | Bryant et al. | |
| 2003/0089161 A1 | 5/2003 | Gysling | |
| 2003/0136186 A1 | 7/2003 | Gysling et al. | |
| 2003/0154036 A1 | 8/2003 | Gysling et al. | |
| 2004/0006409 A1* | 1/2004 | Liljenberg et al. | 700/266 |
| 2004/0016284 A1 | 1/2004 | Gysling et al. | |
| 2004/0069069 A1 | 4/2004 | Croteau et al. | |
| 2004/0074312 A1 | 4/2004 | Gysling | |
| 2004/0144182 A1 | 7/2004 | Gysling et al. | |
| 2004/0167735 A1 | 8/2004 | Rothman et al. | |
| 2004/0194539 A1 | 10/2004 | Gysling | |
| 2004/0199340 A1 | 10/2004 | Kersey et al. | |

FOREIGN PATENT DOCUMENTS

| | | |
|---|---|---|
| EP | 1186868 | 3/2002 |
| GB | 2210169 | 6/1989 |
| WO | WO 93/14382 | 7/1993 |
| WO | WO 99/067629 | 12/1999 |
| WO | PCT 0046583 | 8/2000 |
| WO | WO 0250511 | 6/2002 |
| WO | WO 04063741 | 7/2004 |

OTHER PUBLICATIONS

U.S. Appl. No. 60/402,491, filed Aug. 2002, Gysling et al.

"Sonar-Based Volumetric Flow Meter for Pulp and Paper Applications" by: Daniel L. Gysling and Douglas H. Loose—Dec. 3, 2002.

Sonar-Based Volumetric Flow Meter for Chemical and Petrochemical Applications—by: Daniel L. Gysling and Douglas H. Loose—Feb. 14, 2003.

"Sonar Gets into the Flow" by: Daniel L. Gysling and Douglas H. Loose—Jan. 2004.

"Noise and Vibration Control Engineering Principles and Applications", Leo L. Beranek and Istvan L. Ver, A. Wiley Interscience Publication, pp. 537-541, Aug. 1992.

"Two Decades of Array Signal Processing Research", The Parametric Approach, H. Krim and M. Viberg, IEEE Signal Processing Magazine, Jul. 1996, pp. 67-94.

"Development of an array of pressure sensors with PVDF film, Experiments in Fluids 26", Jan. 8, 1999, Springer-Verlag.

"Viscous Attenuation of Acoustic Waves in Suspensions" by R.L. Gibson, Jr. and M.N. Toksoz.

* cited by examiner

APPARATUS FOR MEASURING PARAMETERS OF A FLOWING MULTIPHASE MIXTURE

CROSS-REFERENCE TO RELATED PATENT APPLICATIONS

This application claims the benefit of U.S. Provisional Application No. 60/439,717 filed Jan. 13, 2003, U.S. Provisional Patent Application, Ser. No. 60/447,498 filed Feb. 14, 2003, and U.S. Provisional Patent Application, Ser. No. 60/440,014 filed Jan. 14, 2003, which are incorporated herein by reference in their entirety.

TECHNICAL FIELD

This invention relates to an apparatus for measuring the parameters of a multiphase flow, and more particularly to an apparatus for measuring the speed of sound propagating in a multiphase mixture to determine parameters, such as mixture quality, particle size, vapor/mass ratio, liquid/vapor ratio, mass flow rate, enthalpy and volumetric flow rate of the flow in a pipe or unconfined space using ultrasonic transducers/sensors.

BACKGROUND ART

In the exhaust of a LPT turbine, the quality of the steam has a significant impact on the efficiency of the turbine. If the steam is too dry, excess energy remains in the steam before it hits the condenser. If the steam is too wet, the excess liquid particles can damage the turbine and degrade the aerodynamics. Typically, the exhaust steam from an LPT turbine is nominally approx. 90% quality, or 10% wetness. It would be advantageous to provide a probe to enable the measurement of the steam quality of LPT turbines.

The knowledge or determination of the different parameters of a process flow comprising a saturated vapor/liquid flow is used to provide feedback of the process to improve quality control of a process or detect problems or needed maintenance of the processing system. One such parameter of the vapor/liquid flow is vapor quality (e.g., steam quality) and "wetness" of the mixture. Vapor quality of a saturated vapor/liquid mixture is defined as the ratio of the mass of the vapor phase to the total mass of the mixture. Conversely, the "wetness" of a saturated vapor/liquid mixture is defined as the ratio of the mass of the liquid phase to the total mass of the mixture.

Saturated mixtures exist at temperatures and pressures at which liquid and vapor phases coexist. The temperatures and pressures at which the liquid and vapor phases coexist lie under the "vapor bubble" (i.e., saturation lines) on a phase diagram. A representative phase diagram for water is shown in FIG. 1. The collection of points known as the saturated liquid line and the collections of points known as the saturated vapor line define the vapor bubble. These two lines connect at, what is termed, the critical point. Saturated mixtures exist only under the vapor bubble. For pressures and temperatures outside of the vapor bubble, the fluid exists as a single phase and the properties of that fluid, such as density, enthalpy, internal energy, etc., are uniquely defined by the pressure and temperature. For common fluids, such as water, these properties are tabulated as functions of pressure and temperatures and are available through a variety of references.

For fluids at pressures and temperatures that lie within the vapor bubble, the fluids represent mixtures of the liquid and vapor phase. Although the properties of both the vapor and liquid phases are well defined (and tabulated for known substances), the properties of the mixture are no longer uniquely defined as functions of pressure and temperature. In order to define the averaged properties of a saturated mixture, the ratio of the vapor and liquid components of the mixture must be defined. The quality of the mixture, in addition to the pressure and temperature, are defined and used to uniquely determine the properties of the mixture.

Measuring the average properties of a mixture is important in many industrial application since it is the mass averaged properties of the working fluid that enter directly into monitoring the thermodynamic performance of many processes. For example, it is the difference in the flux of enthalpy of the steam mixture flowing into and exiting from a turbine that determines the maximum mechanical work that can be extracted from the working fluid, and thus is important to determine component efficiency. However, if the steam entering or exiting the turbine were saturated, pressure and temperature measurement would not be sufficient to determine the specific enthalpy, but rather, a measurement of the quality of the steam would be required to uniquely define the thermodynamic properties of the saturated steam mixture. Note that once the quality and pressure (or temperature) of a saturated mixture is defined, the thermodynamic properties of the mixture are defined through mixing laws provided the properties of the liquid and vapor sates are known.

The present invention provides the means for measuring the speed of sound enables one to determine quality, which in turn enables one to calculate enthalpy, density, and other properties of the mixture. In addition to measuring the specific enthalpy, a measurement of the total mass is also, in general, needed to determine the flux of enthalpy.

There are many other situations where knowing the quality of a saturated mixture is beneficial. For example, in a steam power plant, the quality of the steam within the steam turbine affects blade life. Generally it is desired to operate so the quality is as high as possible throughout the turbine to minimize liquid water drops that will erode the metal blades. Knowing the quality at the turbine inlet and exhaust (or at the exhaust only if the inlet is super-heated) provides a means to monitor the quality throughout the turbine. Also, to monitor plant performance so that it can be operated at optimum conditions and to identify degradation effects, the steam turbine thermal performance must be known. This requires the fluid enthalpy at the inlet and exhaust of each turbine to be known. If the fluid at either or both locations is saturated, pressure and temperature measurements alone will not be enough to determine the enthalpy. However if an additional measurement of quality is made the enthalpy is then defined. In addition, there may be other applications in refrigeration cycles.

The ability to measure the flow rate and composition of the saturated vapor/liquid mixtures within the conduits is an important aspect of any system or strategy design to optimize the performance of a system based on saturated vapor/liquid mixtures. The industry recognizes this, and has been developing a wide variety of technologies to perform this measurement. These include probe based devices, sampling devices, venturis and ultrasonic devices

SUMMARY OF THE INVENTION

Objects of the present invention include providing an apparatus for measuring the speed of sound propagating in a multiphase mixture to determine parameters of the flow in a confined (e.g. pipe, duct), unconfined space or a pipe, for example, using ultrasonic transducers/sensors.

An apparatus for measuring the composition of a mixture flowing through a pipe includes an ultrasonic sensor apparatus disposed along the pipe. The ultrasonic sensor transmits an ultrasonic signal through the mixture and receives the ultrasonic signal, to provide a measured signal indicative of the transit time of the ultrasonic signal through the mixture. The mixture includes particles suspended within a fluid. A processor, responsive to said measured signal, determines the speed of sound propagating through the mixture. Further the processor, responsive to the speed of sound, determines an output signal indicative of the composition of the mixture flowing through the pipe by determining the speed of sound propagating through the mixture as a function of frequency to characterize dispersion properties of the mixture and comparing the dispersion properties of the mixture to a dispersion model of the mixture.

An apparatus for measuring the composition of a mixture flowing through a pipe includes an ultrasonic sensor apparatus disposed along the pipe that transmits an ultrasonic signal through the mixture and receives the ultrasonic signal. The ultrasonic sensor apparatus provides a measured signal indicative of the transit time of the ultrasonic signal through the mixture. The mixture includes particles suspended within a fluid. A processor, responsive to said measured signal, determines the speed of sound propagating through the mixture. Further the processor, responsive to the speed of sound, determines an output signal indicative of the composition of the mixture flowing through the pipe using a dispersion model, wherein the dispersion model is:

$$a_{mix}(\omega) = a_f \sqrt{1 + \cfrac{\varphi_p \rho_p}{\rho_f \left(1 + \omega^2 \cfrac{\rho_p^2 v_p^2}{K^2}\right)}}$$

wherein $a_{mix}$ is the speed of sound propagating through the mixture, $a_f$ is the speed of sound propagating through the fluid, K is a proportionality constant, $\omega$ is frequency in rad/sec, $\phi_p$ is the volumetric phase fraction of the particles, $\rho_p$ is the density of the particles, $v_p$ is the volume of individual particles, and $\rho_r$ is the density of the fluid.

An apparatus for measuring the composition of a mixture flowing through a pipe includes an ultrasonic sensor apparatus disposed along the pipe. The ultrasonic apparatus transmits an ultrasonic signal through the mixture and receives the ultrasonic signal, to provide a measured signal indicative of the transit time of the ultrasonic signal through the mixture. The mixture includes particles suspended within a fluid. A processor, responsive to said measured signal, determines the speed of sound propagating through the mixture. Further the processor, responsive to the speed of sound, determines an output signal indicative of the composition of the mixture flowing through the pipe using a dispersion model. The processor compares at least a transitional frequency range of the dispersion model to determine the average size of the particles in the mixture.

An apparatus for measuring the composition of a mixture flowing through a pipe includes an ultrasonic sensor apparatus disposed along the pipe that transmits an ultrasonic signal through the mixture and receives the ultrasonic signal, to provide a measured signal indicative of the transit time of the ultrasonic signal through the mixture. The mixture includes particles suspended within a fluid. A processor, responsive to said measured signal, determines the speed of sound propagating through the mixture. Further, the processor, responsive to the speed of sound, determines an output signal indicative of the composition of the mixture flowing through the pipe using a dispersion model. The processor compares at least one of the lower frequency range and the transitional frequency range of the dispersion model to determine the phase fraction of the mixture.

A method for measuring the composition of a mixture in a pipe includes measuring the transit time of an ultrasonic signal propagating through the mixture. The mixture includes particles suspended within a fluid. The method further includes determining the composition of the mixture by determining the speed of sound propagating through the mixture as a function of frequency, in response to the measured transit time, to characterize dispersion properties of the mixture and comparing the dispersion properties of the mixture to a dispersion model of the mixture.

A method for measuring the composition of a mixture in a pipe includes measuring the transit time of an ultrasonic signal propagating through the mixture. The mixture includes particles suspended within a fluid. The method further includes determining the composition of the mixture by determining the speed of sound propagating through the mixture as a function of frequency, in response to the measured transit time, to characterize dispersion properties of the mixture and comparing the dispersion properties of the mixture to a dispersion model of the mixture.

A method for measuring the composition of a mixture in a pipe includes measuring the transit time of an ultrasonic signal propagating through the mixture. The mixture includes particles suspended within a fluid. The method further includes determining the composition of the mixture by determining the speed of sound propagating through the mixture in response to the measured transit time, and using a dispersion model. The method also includes comparing at least a transitional frequency range of the dispersion model to determine the average size of the particles in the mixture.

A method for measuring the composition of a mixture in a pipe includes measuring the transit time of an ultrasonic signal propagating through the mixture. The mixture includes particles suspended within a fluid. The method further includes determining the composition of the mixture by determining the speed of sound propagating through the mixture in response to the measured transit time, and using a dispersion model. Also the method includes comparing at least one of the lower frequency range and the transitional frequency range of the dispersion model to determine the phase fraction of the mixture.

The foregoing and other objects, features and advantages of the present invention will become more apparent in light of the following detailed description of exemplary embodiments thereof.

BEST MODE FOR CARRYING OUT THE INVENTION

Figure 2:
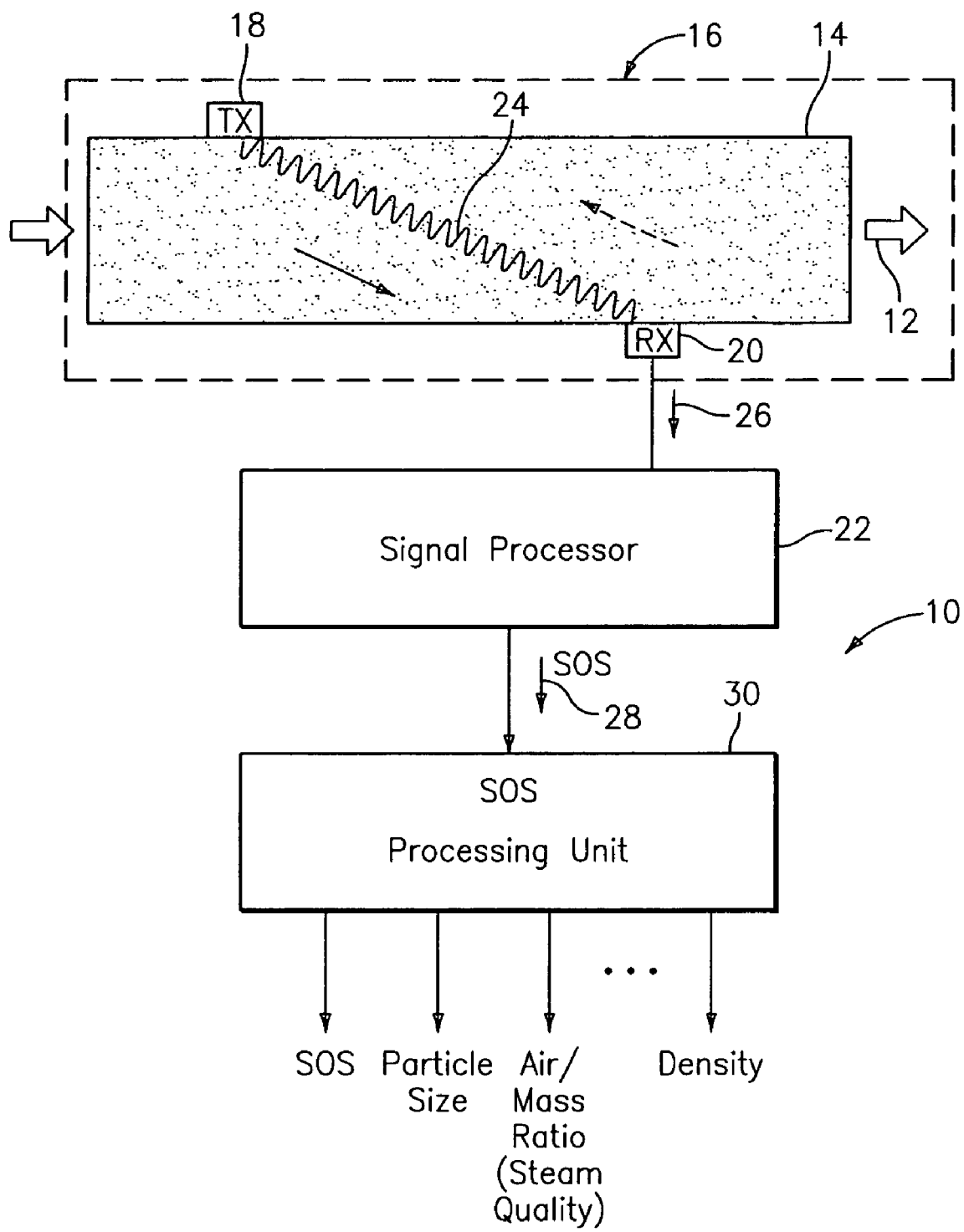
FIG. 2 is a schematic illustration of a probe in accordance with the present invention.
Figure 3:
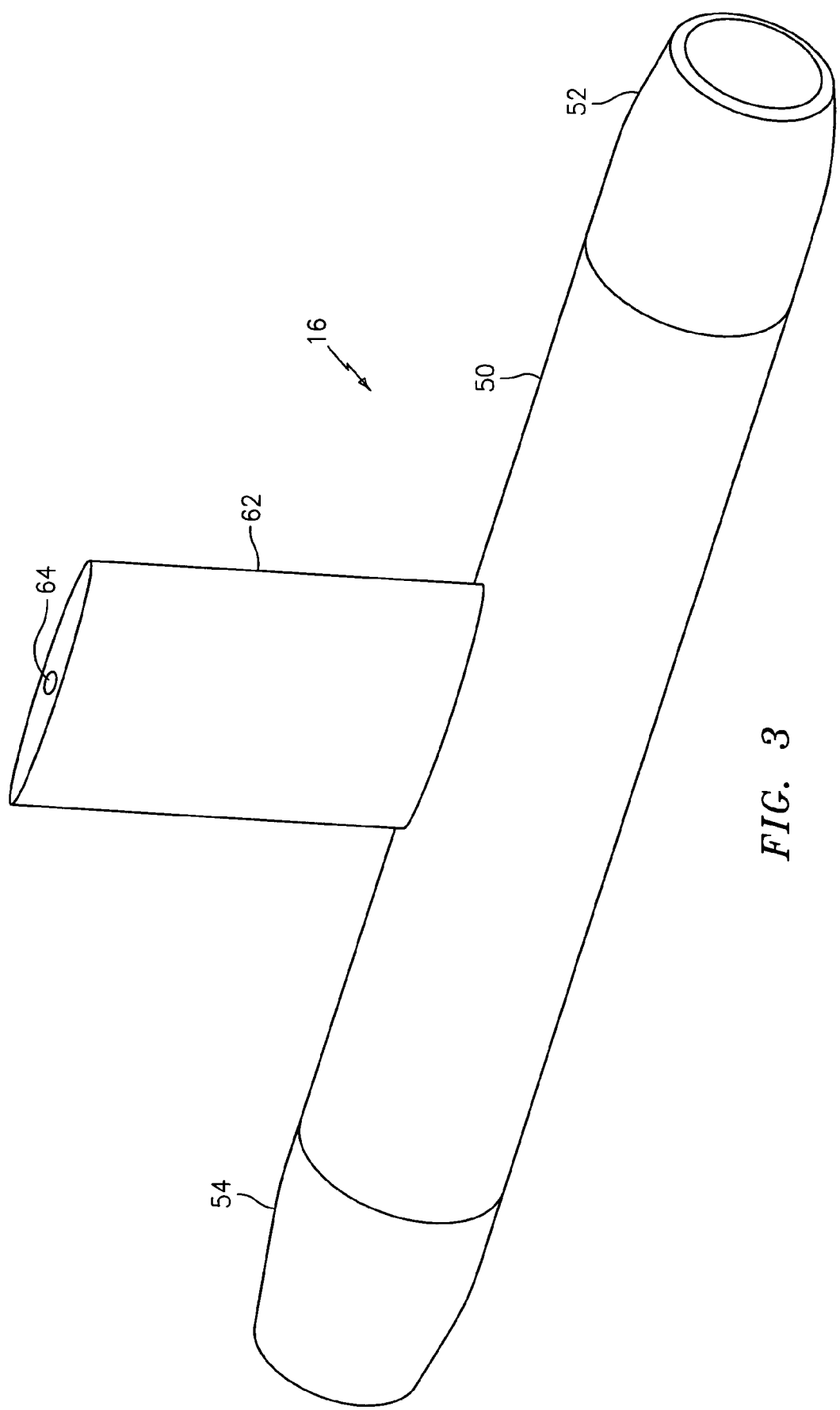
FIG. 3 is a perspective view of a probe in accordance with the present invention.

Referring to FIGS. 2 and 3, a probe, generally shown as 10, is provided to sense and determine specific characteristics or parameters of a multi-phase mixture 12 flowing through a pipe (conduit) or in an unconfined space. The multi-phase mixture may be a two-phase liquid/vapor mixture, a solid/vapor mixture or a solid/liquid mixture, or even a three-phase mixture provided the particles within the fluid are substantially small as will be described hereinafter. One example of a multiphase mixture that can be measured is a saturated vapor/liquid mixture, such as steam. To simplify the description of the present invention, the probe 10 will be described as an apparatus for measuring the parameters of a steam mixture, however, one will appreciate that the probe may be used to measure specific characteristics of a particular multiphase mixture provide the particle disposed therein are small.

As will be described in greater detail, the probe measures the speed of sound propagating through the multiphase mixture flow to determine any one of a plurality of parameters of the flow, such as the steam quality or "wetness", vapor/mass ratio, liquid/solid ratio, the volumetric flow rate, the mass flow rate, the size of the suspended particles, and the enthalpy of the flow.

FIG. 2 illustrates a schematic drawing of the probe 10 that includes a sensing device 16 comprising an ultrasonic transmitter 18 and an ultrasonic receiver 20 disposed axially along the pipe 14, spaced a predetermined distance. In response to a signal processor 22, the transmitter fires an ultrasonic signal 24 to the receiver which then provides a signal 26 to the signal processor indicative of the transit time or time of flight of the ultrasonic signal. The signal processor 22, in response to the transit time measurement signal 26, provides a signal 28 to the speed of sound (SOS) processing unit 30. As will be explained in greater detail hereinafter, the transit time of the ultrasonic signal between the transmitter and the receiver is related to the speed of sound of the fluid 12. The SOS processing unit 30, in accordance with the relationships of the SOS to various parameters of the fluid flow, determines the desired parameters of the fluid flow, such as steam quality, particle size density and mass flow. Some of these relationships are illustrated in FIGS. 8, 9, 10, and 12–15.

Typically, the majority of the mass of the liquid water in the LPT exhaust is contained in small water droplets, having a mean droplet diameter of ~⅓ micron. These saturated steam mixtures can be classified as particulate flows in which small, low volume fraction of relatively incompressible, dense particles are contained in a continuous vapor phase. The particles affect the propagation of the sound through the mixture in a frequency dependent manner. Models of this propagation is described in U.S. patent application Ser. No. 10/349,716 (CC-0579), and U.S. patent application Ser. No. 10/376,427 (CC-0596), which are both incorporated herein by reference. In these models, the sound speed of the mixture if a function of frequency and related to the volumetric phase fraction, viscousity and drag coefficient, and fluid density and particle density and sound speed, which will be described in greater detail hereinafter.

Figure 10:
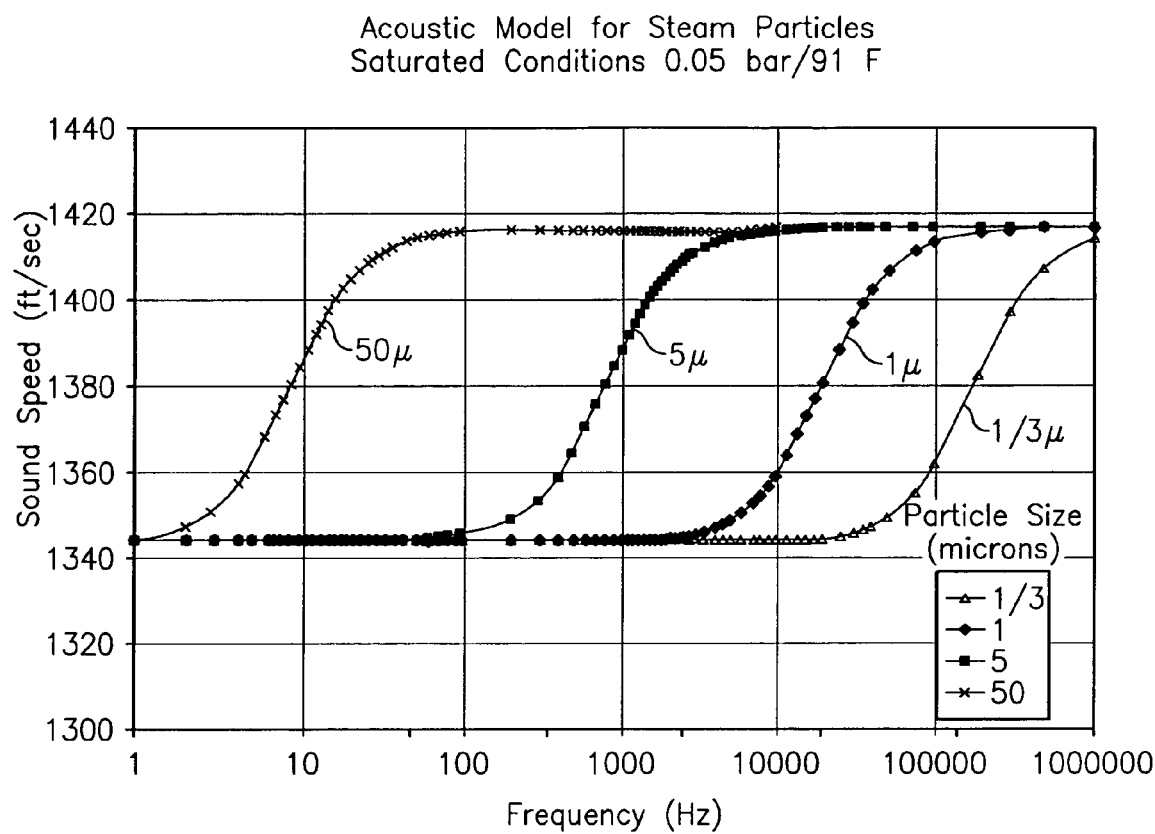
FIG. 10 is a plot of sound speed as a function of frequency for vapor/liquid mixtures with varying particle size, in accordance with the present invention.

Referring to FIG. 10, the frequency behavior can be categorized into three frequency regimes. In the low frequency regime, or quasi-steady regime, there is negligible slip between the particles and the gases during the propagation of the acoustic waves. In this regime, the liquid particles essential mass load the gaseous phase. In this quasi-steady regime the sound speed asymptotes to the quasi-steady value which is directly related to the quality of mixture.

In the high frequency regimes, the particles essentially no longer participate in the propagation of the acoustic waves. The acoustic oscillations are too high frequency to accelerate and decelerate the particles, and the speed of propagation asymptotes to that of the gaseous phase in isolation.

The quasi-steady and high frequency regimes are separated by a transitional regime in which the speed of propagation is highly dependent on frequency. Herein, the transitional frequency is defined as the frequency at which the speed of propagation is midway between the quasi steady propagation velocity and the high frequency propagation velocity. The transitional frequency is strongly affected by particle size. For a given steam mixture, the transitional frequency scales with the square of the inverse of particle size.

Figure 17:
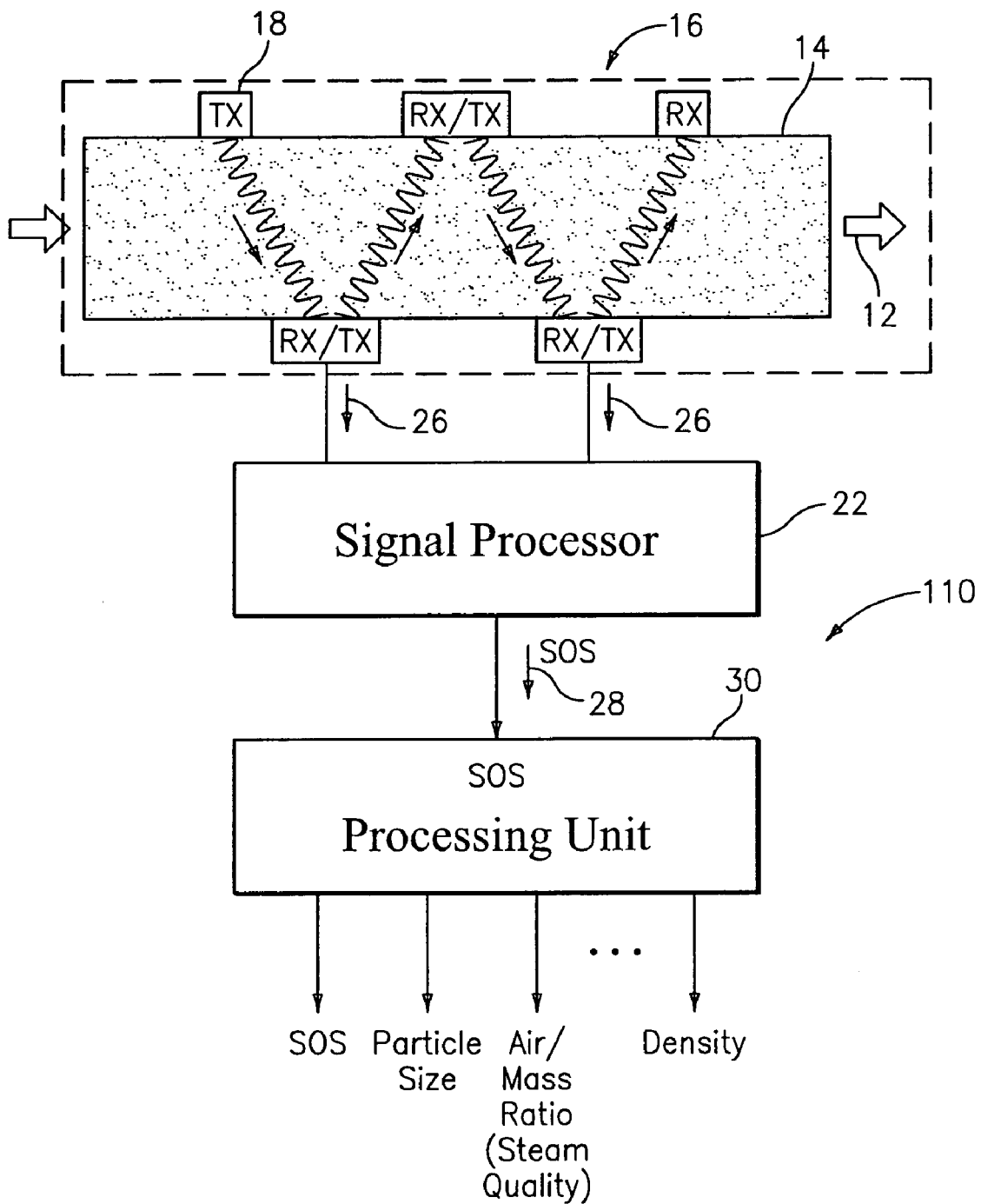
FIG. 17 is a schematic illustration of another embodiment of a probe in accordance with the present invention.

The present invention utilizes the transit time method to determine the dispersive properties of steam mixtures to characterize steam quality and particle size. The invention further contemplates using the sing around method as shown in FIG. 17 to determine the dispersive properties.

In addition to influencing the dispersive properties of the mixture, scattering of acoustic waves by the particles, which by impeding propagation of acoustics through the mixture, can adversely affect the ability of transit time devices to effectively measure the speed of sound of inhomogeneous mixtures.

Figure 1:
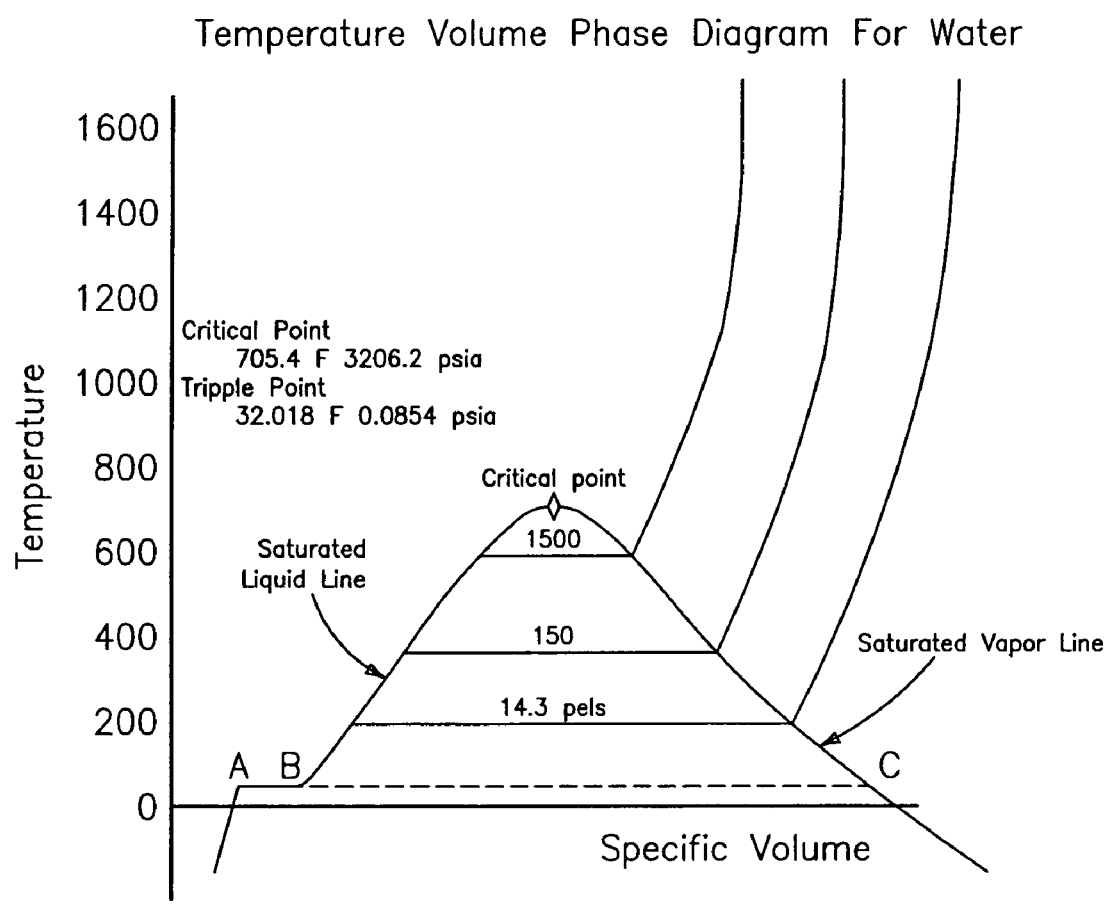
FIG. 1 is a representative phase diagram for water.
Figure 18:
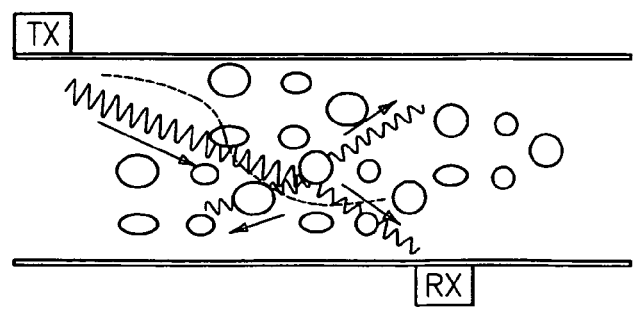
FIG. 18 is a graphical diagram of an ultrasonic signal scatters when contacting large particles in the flow in accordance with the present invention.

Acoustic methods, which rely on transmitting and receiving acoustic waves, can encounter difficulties with inhomogeneous flows due to scattering of the acoustics by the inhomogenieities. The scattering effect is shown schematically in FIG. 18. This typically occurs when the acoustic wavelength approaches the length scale (i.e., size) of the inhomogenieities. If the wavelength of the acoustics is several orders of magnitude greater than the length scale of the acoustics, little scattering occurs as shown in FIG. 1.

Figure 19:
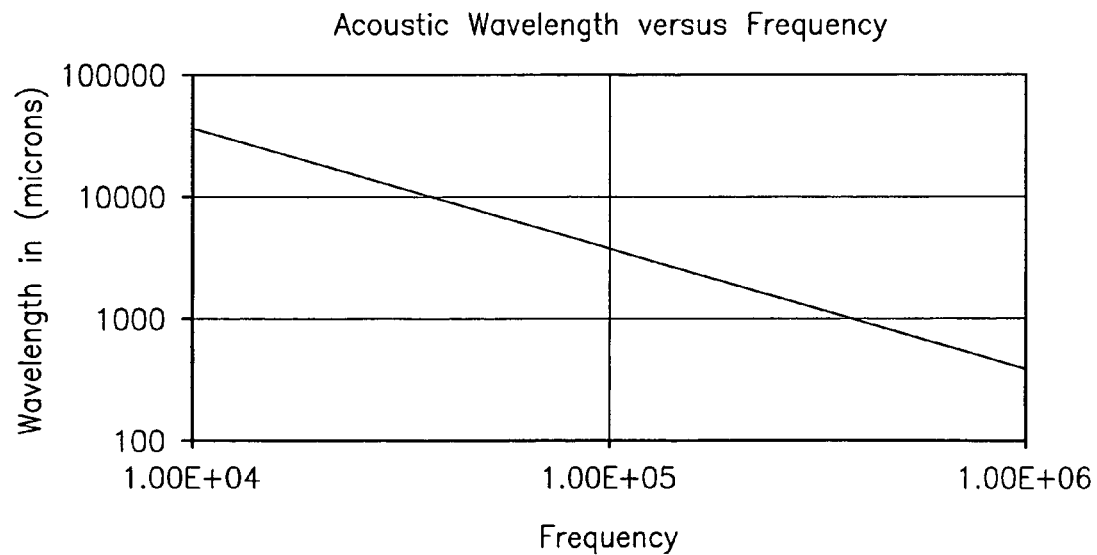
FIG. 19 is a plot the acoustic wavelength versus the frequency in accordance with the present invention.
Figure 11:
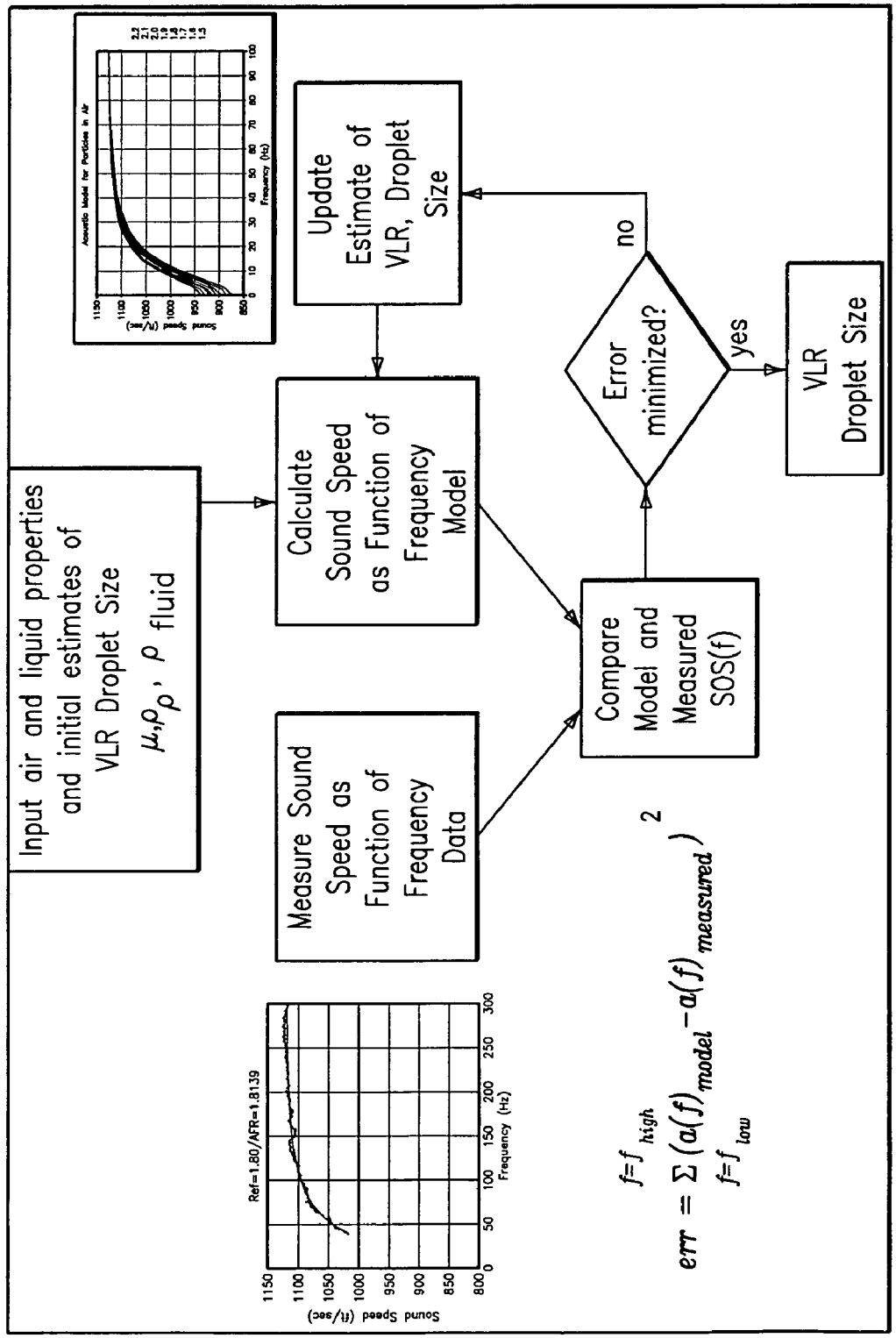
FIG. 11 is a flow diagram of an optimization procedure employed to determine vapor-to-liquid ratio and droplet size from analytical model and experimentally determined dispersive speed of sound data in accordance with the present invention.

The wavelength of acoustics traveling in a mixture with a nominal sound speed of 1200 fee/sec—representative of the speed of sound in slightly wet steam and the exhaust of an LP turbine is shown in FIG. 19. As shown, the wavelength of the sound in the range of 10,000 Hz to 1,000,000 Hz is several orders of magnitude larger than the diameter of the steam particles for steam representative of conditions at the exhaust of an LPT.

Based on the analysis herein, a transmitter and receiver capable of operating over a frequency range of 10,000 to 1,000,000 Hz would be capable of effectively measuring the dispersive properties of steam at the exhaust of LP for steam with particle size of approximately 1 micron and smaller. The same device would not be effective for steam with particle sizes 5 microns or larger. For mixtures with these particle sizes and larger, transmitters and receivers capable of operating at significantly lower frequencies would be required.

For example, based on the dispersive properties given in FIG. 10, to effectively measure the dispersive properties of a steam mixture with particles (droplets) on the order of 50 microns, the acoustic transmitters and receivers would have to be capable of launched and deterring waves of frequency well below 100 Hz.

Figure 4A:
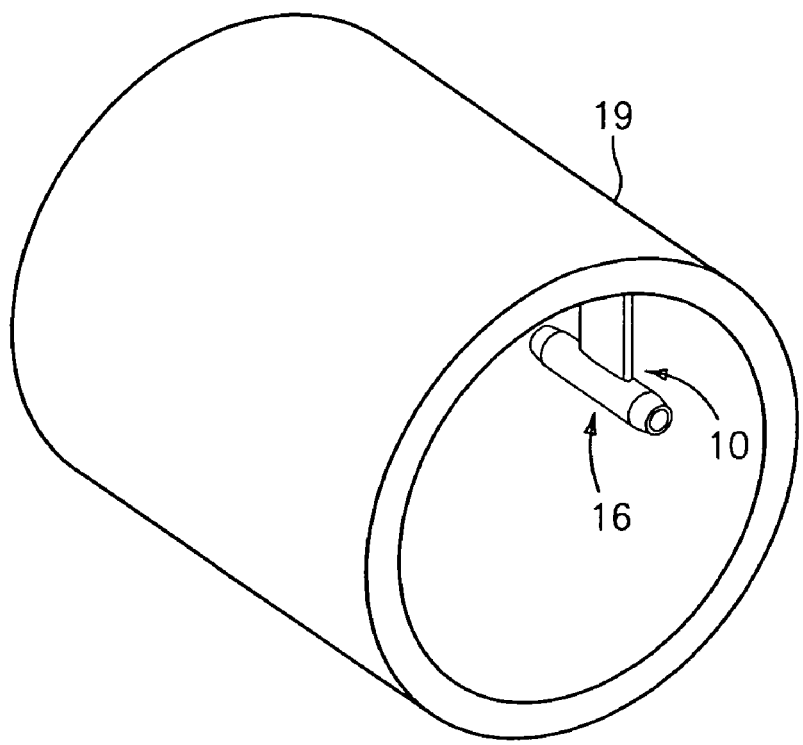
FIG. 4a is a perspective view of a probe embodying the present invention mounted within a pipe having circular cross-section in accordance with the present invention.
Figure 4B:
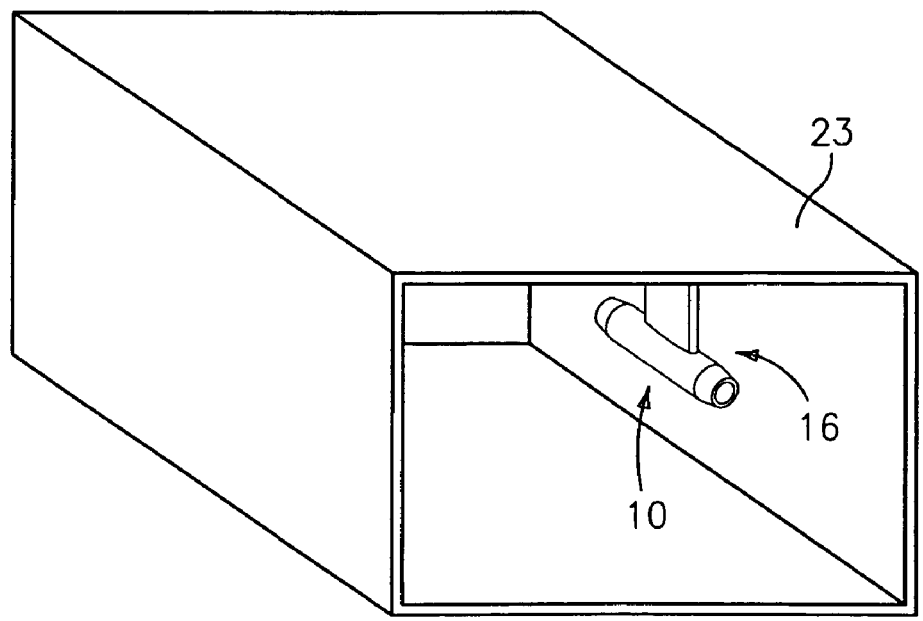
FIG. 4b is a perspective view of a probe embodying the present invention mounted within a duct having rectangular cross-section in accordance with the present invention.
Figure 5:
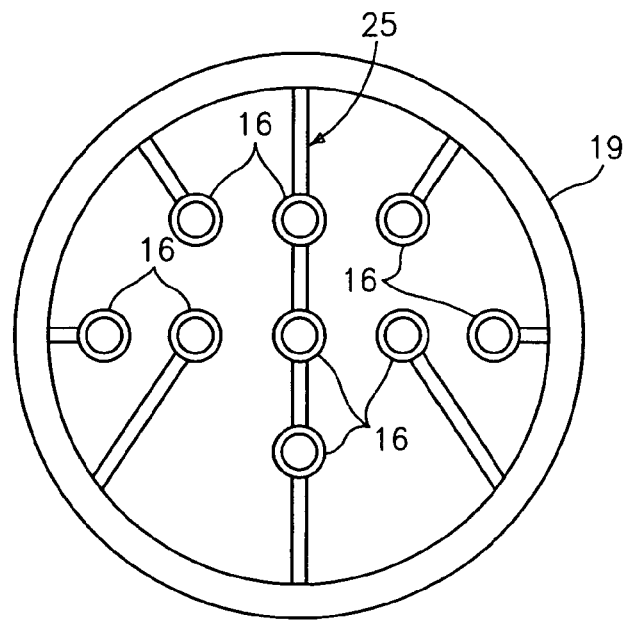
FIG. 5 is a cross-sectional view of a plurality of probes disposed within a pipe for characterizing the flow pattern of the flow passing through the pipe in accordance with the present invention.

The probe 10 may be used a number of different ways. For example as shown in FIGS. 4a and 4b, the sensing device 16 of the probe may be mounted within a pipe 19 or duct 23, respective to measure the fluid flow or mixture passing therethrough. The probe 10 is particularly useful for large diameter pipes or ducts having a large cross-sectional area, such as smokestacks, exhaust ducts or HVAC systems. The utility of the probe is especially evident for measuring the flow of a multiphase mixture 12 that is not confined within piping or ducting. For example, the probe may be mounted within a gas turbine to measure the steam "wetness" or other parameters of the steam exiting the exhaust duct of the steam or LPT turbine.

Figure 6:
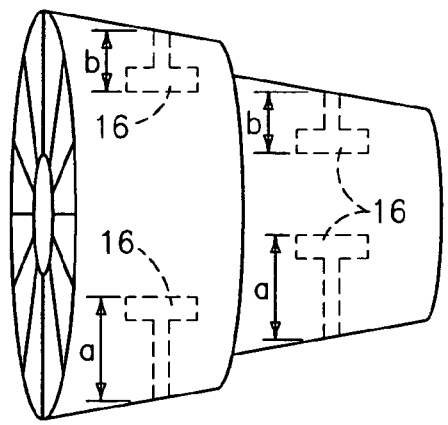
FIG. 6 is a side view of a steam turbine having a plurality of probes disposed at different stages of the turbine and a different depths within each stage in accordance with the present invention.

The probe 10 is particularly useful in characterizing the pattern of the flow 12 within a confined space (e.g., a pipe 19, duct 21) or unconfined space. For example as shown in FIG. 6, one or more sensing devices 16 of respective probes may be disposed at different locations across the area of the flow 12. The data provided by each of the probes and the known location of the probe enables one to characterize the flow pattern. For example, one probe may be disposed adjacent to the wall of a pipe 19 and another probe may be disposed at a central position within the pipe to characterize the velocity and vapor/mass (e.g. steam wetness) at the two locations. One will appreciate that any number of sensing devices 16 may be disposed at number of locations within the flow.

The invention also contemplates a probe having a plurality or array of interconnected sensing devices 16 at 25 that extends across the flow 12 in a single plane or disposed in different planes of the flow. In other words, the sensing devices 16 of the probes 10 may be disposed at different locations along the flow 12. For example as shown in FIG. 6, probes may be disposed at different stages of a gas steam turbine at different locations at each stage. The probe may be used to measure the steam wetness at each stage at different location or depth from the walls of the turbine within each stage to measure the efficiency of the turbine or aid with the design of the turbine.

Figure 7:
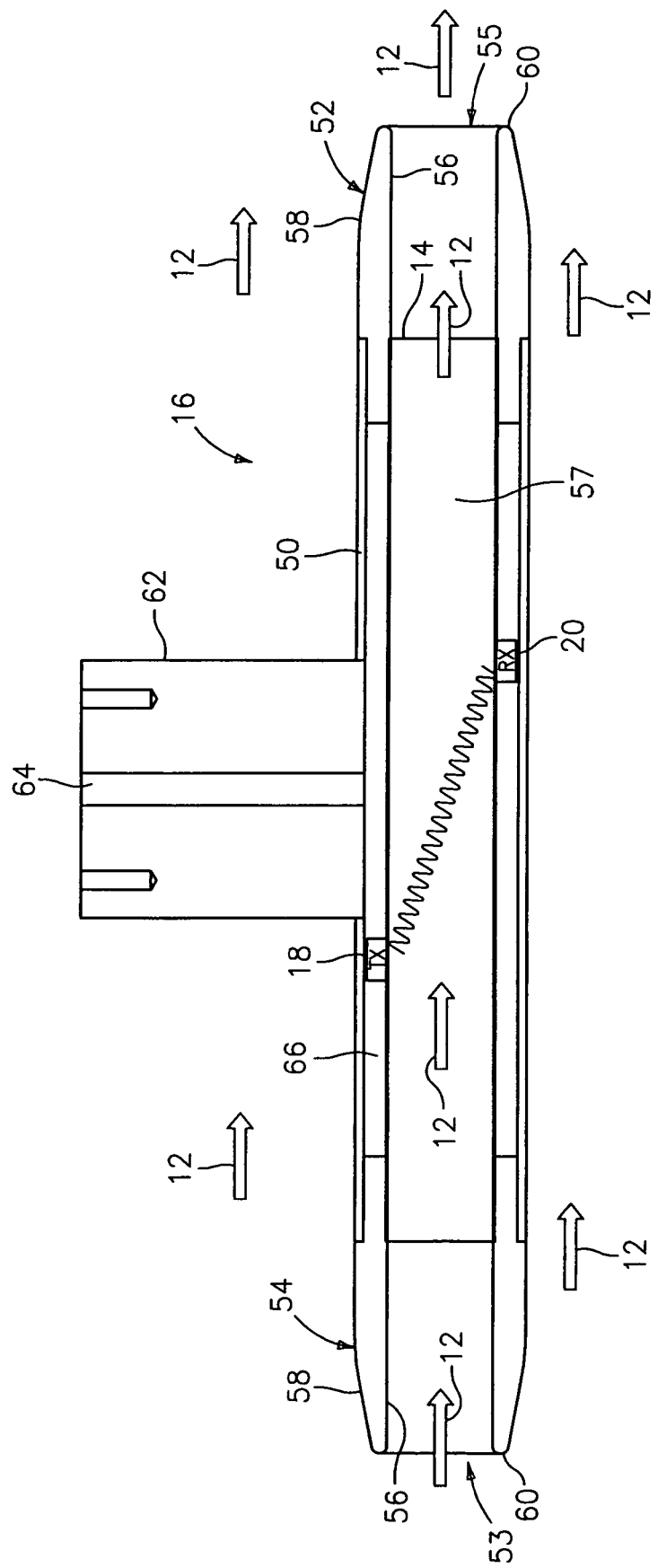
FIG. 7 is a cross-sectional view of a probe in accordance with the present invention.

Referring to FIGS. 2, 3 and 7, in one embodiment of the present invention, the sensing device 16 of the probe 10 includes an inner tube 14 disposed within a tubular, outer housing 50 to provide an input port 53 and output port 55 for the flow 12 to pass through. The inner tube is generally cylindrical in shape having an axial bore 57 with a circular cross-section. The invention, however, contemplates that the inner tube may be of any shape or cross-sectional shape, such as squares, oval rectangular or any other polygonal shape. The cross-sectional shape may even be different along the length of the inner tube. The outer diameter of the inner tube is approximately one inch, but the diameter may be of any length.

A pair of end caps 52,54 is disposed at the respective ends of the inner tube 14 and outer housing 50 to maintain and support the tube coaxially within the housing. The housing protects the array of sensors 18–21 disposed along the tube from the flow 12, and also acts as an insulator or isolator to prevent external acoustic and/or unsteady pressure disturbances from affecting the sensors 18-21. The end caps have a central bore 56 with a inner diameter substantially the same as the inner diameter of the tube 14. The outer surface 58 of the end caps are tapered and the outer ends 60 are rounded to provide an aerodynamic profile to reduce the drag of the flow (e.g., steam) over the probe 10 to reduce the wind resistance and stresses thereon. The aerodynamic profile also reduces the disturbance of the flow of the fluid or mixture. The aerodynamic characteristics are particularly important for high speed steam flow (e.g., 0.7 Mach), such as steam exiting a gas turbine exhaust.

While the sensing device 16 has a pair of end caps 52,54 as shown best in FIG. 7, the invention completes a sensing device 16 having no discrete end caps and that the inner tube 14 extends the length of sensing device of the probe 10.

The embodiment of the sensing device 16 shows a single input and output port 53,55, however, the invention contemplates that the sensing device may have a plurality of input ports and/or output ports that feed into and out of the central portion of the tube 14 where the sensors array 18–21 are disposed. While contemplated, one will appreciate that additional drag may be place upon the sensing device 16 and additional disturbance to the flow 12.

The sensing device 16 of the probe 10 further includes a fin-shaped support structure 62 extending from the center of the housing 50 for mounting the sensing device to a wall or other support, as shown in FIGS. 3–6. The support structure 62 includes a bore 64, disposed therethrough to communicate with the space 66 disposed between the tube 14 and the housing 50. The bore 64 provides a means to run the conductors of the ultrasonic sensors ?? to the processing unit 24, as best shown in FIG. 2. The support structure 62 is oriented to reduce wind resistance to minimize disturbance of the steam flow.

Steam driven turbines are a major source of electrical power world wide. At present, there are no real time, operationally effective methods to monitor the quality of the steam as it drives the generators. Ideally, the industry would like to extract the maximum amount of energy from the steam as it passes through the turbine system thus reducing it to water; however, as water droplets form from the steam, they induce erosion and wear in the turbine blades requiring expensive maintenance. Thus a balance between the energy extracted from and the amount of water entrained in the steam must be met.

Standard temperature and pressure cannot uniquely determine the wetness, i.e. the amount of water in the steam, when both phases coexist. The present invention uses speed of sound measurements to determine wetness of saturated steam using dispersion calculations. In non-nuclear power generation plants, the steam is super heated, and thus comprises only one phase, for each process step except the Low Pressure (LP) Turbine Exhaust. At this exhaust, the wet steam is traveling at speeds in the range 0.5 to 0.7 Mach (Ma).

Referring to FIG. 2, a probe 10 embodying the present invention is provided that measures at least one parameter/characteristic of a multiphase mixture 12 such as a saturated vapor/liquid mixture 12 of liquid droplets suspended within a continuous vapor/gas, for example, flowing within a pipe 19, duct 21 or flowing unconfined (see FIGS. 3–6). The probe may be configured and programmed to measure the speed of sound propagating through the flow 12. Depending on the configuration or embodiment, the probe can measure at least one of the following parameters of the flow 12: the wetness or steam quality (volumetric phase fraction), the volumetric flow rate, the size of the liquid particles, the mass flow, the enthalpy and the velocity of the mixture. To determine any one of these parameters, the probe 10 measures the transit time of an ultrasonic signal through the fluid 12 between an ultrasonic transmitter 18 and receiver 20.

In this case, the wavelength of the measured acoustic signal determines the sensor spacing. The desired wavelength of the measured acoustic signal is dependent upon the dispersion of particles in the mixture flow, which is dependent on the particle size, which will be described in greater detail hereinafter The probe 10 can be used in any application that carries liquid droplets suspended in a vapor/gas through a pipe, such as in paper/pulp, petroleum and power generation applications. For example, the present invention is well suited to measure the parameters (e.g. vapor/liquid ratio, particle size) for power generation systems.

As one example, the present invention will be discussed in the context of a steam delivery system for power generation, but one will appreciate that the probe 10 can be applied to any number of other applications, as discussed hereinbefore.

As described hereinbefore, the probe 10 of the present invention may be configured and programmed to measure and process the transit time of an ultrasonic signal between an ultrasonic transmitter 18 and receiver 20 propagating through the mixture to determine parameters of the mixture flow 12. One such probe 10 is shown in FIG. 3 that measures the speed of sound (SOS) of one-dimensional sound waves propagating through the vapor/liquid mixture to determine the composition the mixture, namely the "wetness" or steam quality of the mixture. The probe is also capable of determining the average size of the droplets, velocity of the mixture, enthalpy, mass flow, steam quality or wetness, density, and the volumetric flow rate of the mixture. It is known that sound propagates through various mediums at various speeds in such fields as SONAR and RADAR fields. The speed of sound of a mixture within the inner tube 14 may be determined using a number of known techniques, such as those set forth in U.S. patent application Ser. No. 09/344,094, entitled "Fluid Parameter Measurement in Pipes Using Acoustic Pressures", filed Jun. 25, 1999, and U.S. patent application Ser. No. 10/007,749, entitled "Fluid Parameter Measurement in Pipes Using Acoustic Pressures", filed Nov. 7, 2001, each of which are incorporated herein by reference. The present invention utilizes at least one probe 10 to determine various parameters of the saturated vapor/liquid mixture, wherein one of the parameters is the speed at which sound travels within in the flow, as will be more fully described herein below.

In accordance with the present invention, the speed of sound propagating through the vapor/liquid mixture 12 is measured by passively listening to the flow with an array of unsteady pressure sensors to determine the speed at which one-dimensional compression waves propagate through a vapor/liquid mixture contained within the tube 14.

For relatively well-mixed vapor/liquid mixtures in which the liquid phase exists as small droplets within a continuous gas phase, the flow can be termed mist flow. Assuming that the droplets of the vapor/liquid mixture are small enough and the acoustic frequencies and the frequencies of perturbations associated with the acoustics are low enough for the droplets of liquid to exhibit negligible slip (both steady and unsteady), the sound speed can be assumed to be substantially non-dispersive (that is constant with frequency) and the volumetric phase fraction of the mixture could be determined through the Wood equation:

$$\rho_{mix} = \sum_{i=1}^{N} \phi_i \rho_i$$

$$\frac{1}{\rho_{mix} a_{mix}^2} = \sum_{i=1}^{N} \frac{\phi_i}{\rho_i a_i^2}$$

$$\sum_{i=1}^{N} \phi_i = 1$$

For one-dimensional waves propagating within a vacuum backed tube 14 (or a tube immersed in large volume of low impedance fluid such as air at atmospheric conditions), the compliance introduced by the tube (in this case a circular tube of modulus E, radius R and wall thickness t) reduces the measured sound speed from the infinite dimensional sound speed. The effect of the conduit is given by the following relationship:

$$\frac{1}{\rho_{mix} c_{measured}^2} = \frac{1}{\rho_{mix} c_{mix}^2} + \sigma \text{ where } \sigma \equiv \frac{2R}{Et}$$

Utilizing the relations above, the speed at which sound travels within the representative vapor/liquid mixture is a function of vapor/liquid mass ratio. The effect of increasing liquid fraction, i.e. decreasing vapor/liquid ratio, is to decrease the sound speed. Physically, adding liquid droplets effectively mass loads the mixture, while not appreciably changing the compressibility of the air. Over the parameter range of interest, the relation between mixture sound speed and vapor/liquid ratio is well behaved and monatomic.

While the calibration curves based on predictions from first principles are encouraging, using empirical data mapping from sound speed to vapor/liquid ratio may result in improved accuracy of the present invention to measure the vapor/liquid fractions of the mixture.

The sound speed increases with increasing frequency and asymptotes toward a constant value. The sound speed asymptote at higher frequency is essentially the sound speed of air only with no influence of the suspended liquid droplets. Also, it is apparent that the sound speed of the vapor/liquid mixture has not reached the quasi-steady limit at the lowest frequency for which sound speed was measured. The sound speed is continuing to decrease at the lower frequency limit. An important discovery of the present invention is that the speed at which sound propagates through droplets suspended in a continuous vapor is said to be dispersive. As defined herein, the speed at which acoustic waves propagate through dispersive mixtures varies with frequency.

For accurately measuring sound speeds at ultra-low frequencies, the data suggests that utilizing a quasi-steady model to interpret the relationship between sound speed, measured at frequencies above those at which the quasi-steady model is applicable, and the liquid-to-vapor ratio would be problematic, and may, in fact, be impractical. Thus, the key to understanding and interpreting the composition of vapor/liquid mixtures through sound speed measurements lies in the dispersive characteristics of the vapor/liquid mixture.

In accordance with the present invention the dispersive nature of the system utilizes a first principles model of the interaction between the vapor and liquid droplets. This model is viewed as being representative of a class of models that seek to account for dispersive effects. Other models could be used to account for dispersive effects without altering the intent of this disclosure (for example, see the paper titled "Viscous Attenuation of Acoustic Waves in Suspensions" by R. L. Gibson, Jr. and M. N. Toksöz), which is incorporated herein by reference. The model allows for slip between the local velocity of the continuous vapor phase and that of the droplets. The drag force on the droplets by the continuous vapor is modeled by a force proportional to the difference between the local vapor velocity and that of the liquid droplets and is balanced by inertial force:

$$F_{drag} = K(U_f - U_p) = \rho_p v_p \frac{\partial U_p}{\partial t}$$

where K=proportionality constant, $U_f$=fluid velocity, $U_p$=liquid droplet velocity, $\rho_p$=liquid droplet density and $v_p$=particle volume.

The effect of the force on the continuous vapor phase by the liquid droplets is modeled as a force term in the axial momentum equation. The axial momentum equation for a control volume of area A and length $\Delta x$ is given by:

$$P_x - P_{x+\Delta x} - K(U_f - U_p)\left\{\frac{\phi_p \Delta x}{v_p}\right\} = \frac{\partial}{\partial t}(\rho_f U_f \Delta x)$$

where P=pressure at locations x and $\Delta x$, $\phi_p$=volume fraction of the liquid droplets, $\rho_f$=vapor density.

The droplet drag force is given by:

$$F_{drag} = K(U_f - U_p) = C_d A_p \frac{1}{2} \rho_f (U_f - U_p)^2$$

where $C_d$=drag coefficient, $A_p$=frontal area of liquid droplet and $\rho_f$=vapor density.

Using Stokes law for drag on a sphere at low Reynold's number gives the drag coefficient as:

$$C_d = \frac{24}{Re} = \frac{24\mu}{\rho_f (U_f - U_p) D_p}$$

where $D_p$=droplet diameter and $\mu$=vapor viscosity.

Solving for K in this model yields:

$$K = 3\pi\mu D_p$$

Using the above relations and 1-dimensional acoustic modeling techniques, the following relation can be derived for the dispersive behavior of an idealized vapor/liquid mixture.

$$a_{mix}(\omega) = a_f \sqrt{\frac{1}{1 + \frac{\varphi_p \rho_p}{\rho_f \left(1 + \omega^2 \frac{\rho_p^2 v_p^2}{K^2}\right)}}}$$

In the above relation, the fluid SOS, density ($\rho$) and viscosity ($\phi$) are those of the pure phase fluid, $v_p$ is the volume of individual droplets and $\phi_p$ is the volumetric phase fraction of the droplets in the mixture.

Figure 8:
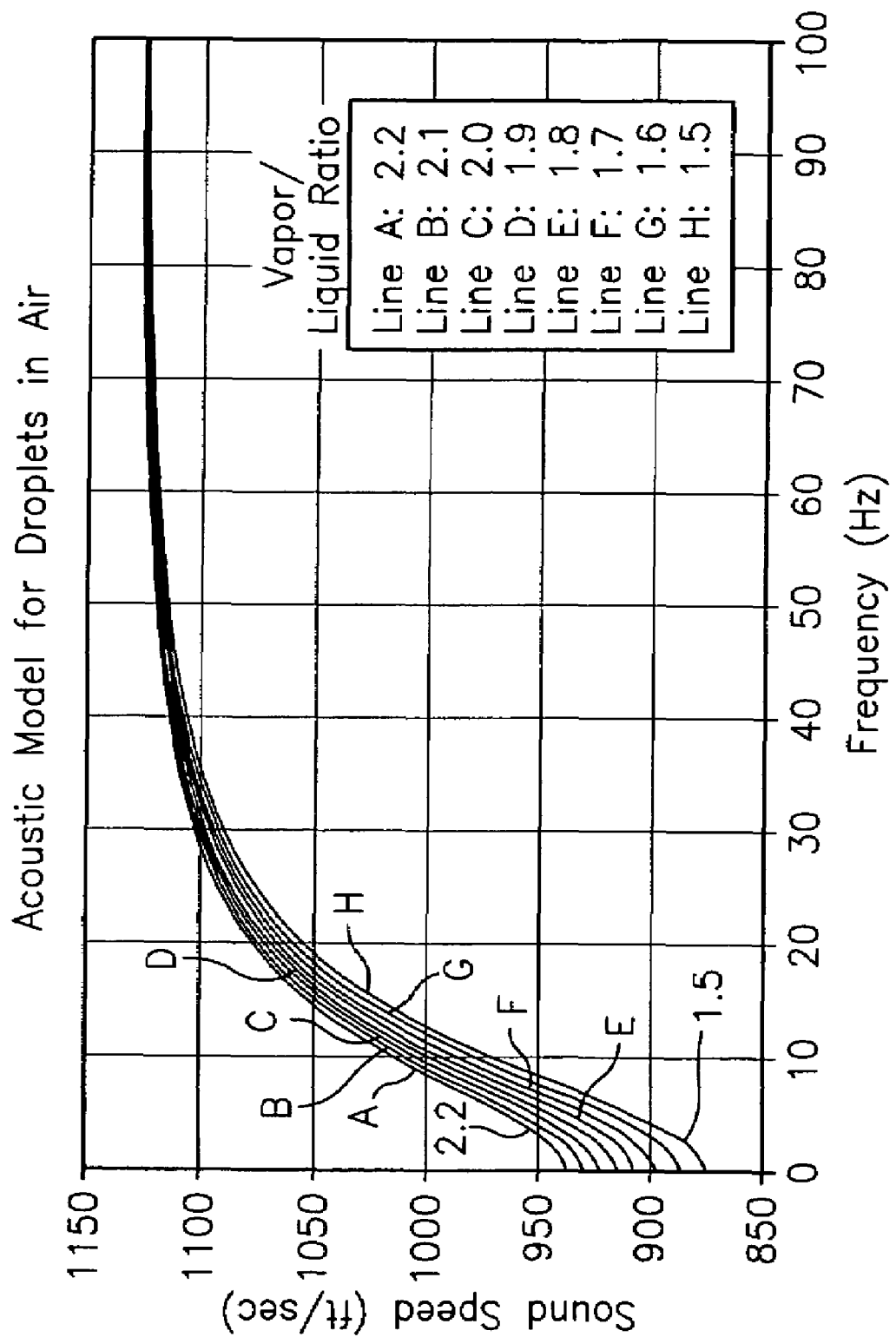
FIG. 8 is a plot of sound speed as a function of frequency for vapor/liquid mixtures with fixed droplet size (50 mm) and varying vapor-to-liquid mass ratio in accordance with the present invention.
Figure 9:
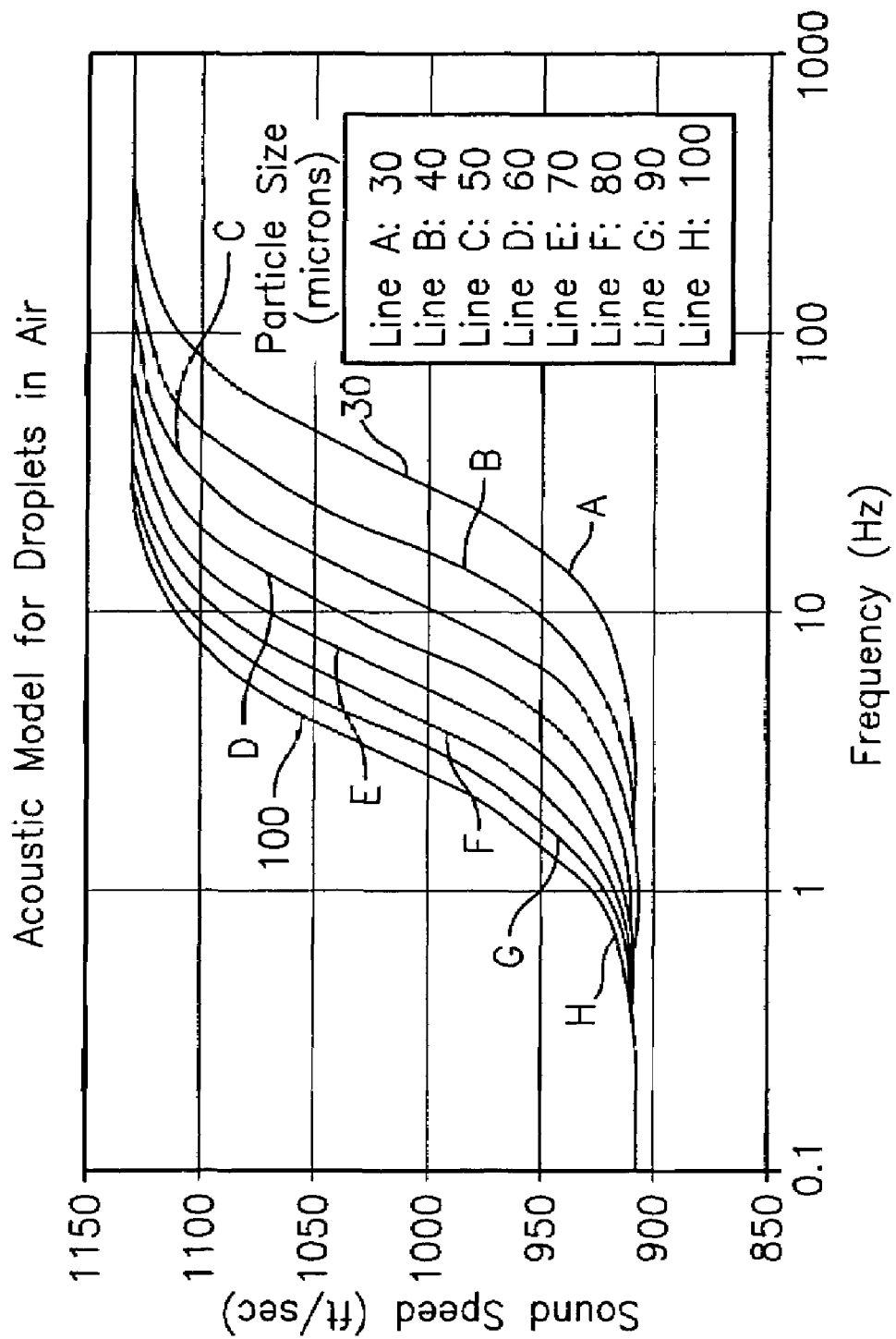
FIG. 9 is a plot of sound speed as a function of frequency for vapor/liquid mixtures with varying particle size where the vapor-to-liquid mass ratio is equal to 1.8 in accordance with the present invention.

Two parameters of primary interest in steam measurements are droplet size and liquid-to vapor mass ratio (i.e., steam quality or steam wetness). To this end, it is of interest to examine the dispersive characteristics of the mixture as a function of these two variables. FIGS. 8 and 9 show the dispersive behavior for vapor/liquid mixtures with parameters typical of those used in steam flow systems.

In particular FIG. 8 shows the predicted behavior for nominally 50 µm size liquid droplets in vapor for a range of liquid-to-vapor ratios. As shown, the effect of liquid-to-vapor ratio is well defined in the low frequency limit. However, the effect of the liquid-to-vapor ratio becomes indistinguishable at higher frequencies, approaching the sound speed of the pure air at high frequencies (above ~100 Hz).

Similarly, FIG. 9 shows the predicted behavior for a vapor/liquid mixture with a liquid-to-vapor ratio of 1.8 with varying liquid droplet size. This figure illustrates that liquid droplet size has no influence on either the low frequency limit (quasi-steady ) sound speed, or on the high frequency limit of the sound speed. However, droplet size does have a pronounced effect in the transition region.

Figure 12:
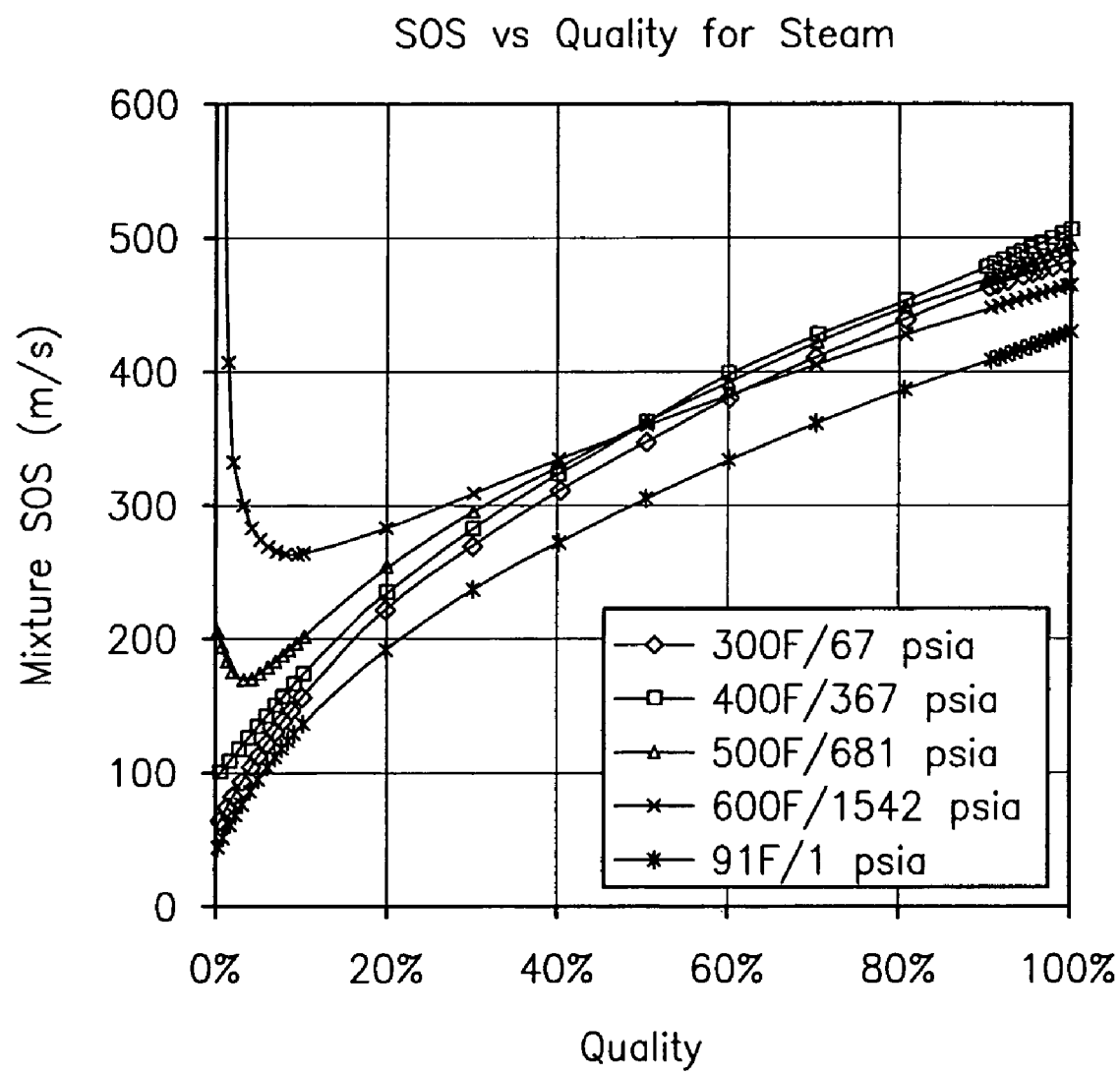
FIG. 12 is a plot of the speed of sound propagating through a saturated vapor/liquid mixture having varying temperature and pressures versus quality of the mixture, in accordance with the present invention.
Figure 13:
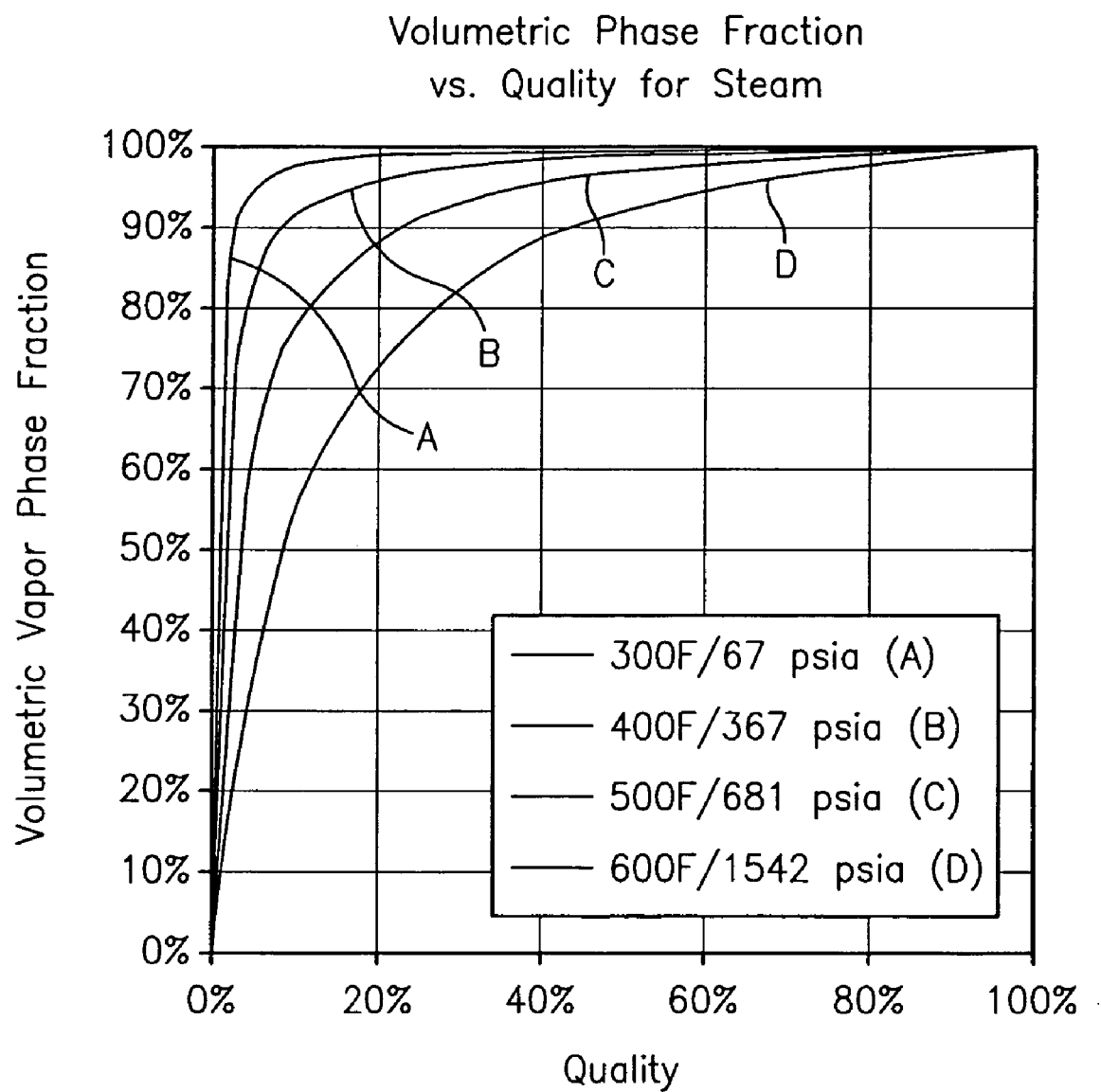
FIG. 13 is a plot of the volumetric vapor phase fraction for vapor/liquid mixtures having varying temperature and pressures versus quality of the mixture, in accordance with the present invention.

FIGS. 8 and 9 illustrate an important aspect of the present invention. Namely, that the dispersive properties of mixtures of droplets suspended in a continuous vapor can be broadly classified into three frequency regimes: low frequency range, high frequency range and a transitional frequency range. Although the effect of droplet size and liquid-to-vapor ratio are inter-related, the predominant effect of liquid-to-vapor ratio is to determine the low frequency limit of the sound speed to be measured and the predominate effect of droplet size is to determine the frequency range of the transitional regions. As droplet size increases, the frequency at which the dispersive properties appear decreases. For typical steam applications, this transitional region begins at fairly low frequencies, ~2Hz for 50 μm size particles.

In the low frequency regime, the liquid droplets exhibit negligible slip with the vapor. The frequency range for which the no-slip, quasi-steady approximation is valid is a function of a variety of parameters including droplet size, continuous phase viscosity, droplet shape and droplet density.

The quasi-steady sound speed is given by the low frequency limit of the above relation, where VLR is vapor/liquid ratio:

$$a_{mix}(\omega \to 0) = a_f * \sqrt{\frac{1}{1 + \frac{\varphi_p \rho_p}{\rho_f}}} \cong a_f * \sqrt{\frac{1}{1 + \frac{1}{VLR}}}$$

Note that droplet size does not affect the low frequency limit of the sound speed.

Similar to FIG. 9, FIG. 10 shows the predicted behavior for a saturated vapor/liquid mixture with a liquid-to-vapor ratio with varying droplet size. Specifically, the particle sizes of three different mixtures include 50 um, 20 um and 1 um. The transitional frequency range of the mixture having 50 um droplets is approximately 3–13 Hz, a central frequency ($f_{1/2}$) of approximately 8 Hz. The transitional frequency range of the mixture having 20 um droplets is approximately 11–110 Hz, a central frequency ($f_{1/2}$) of approximately 60 Hz. The transitional frequency range of the mixture having 1 um is approximately 8–80 KHz, a central frequency ($f_{1/2}$) of approximately 40 degrees. As shown, the droplet size greatly influences the dispersion characteristics of the saturated vapor/liquid mixture. The transistion from the quasi-steady state to the high frequency regime scales inversely with the square of the droplet diameter. As discussed hereinbefore, the dispersion characteristics set the frequency requirements for measuring the speed of sound propagating through the mixture to measure parameters of the mixture.

The frequency of the speed of sound that is detected for a particular mixture sets the wavelength of interest. The wavelength is the inverse of the frequency, and therefore, the higher the frequency, the shorter the wavelength and vice versa. As described hereinbefore, the aperture should be at least a significant fraction of the length of the wavelength of the speed of sound of interest. A vapor/liquid mixture having droplets of approximately 3 um has a central frequency ($f_{1/2}$) of approximately 3 KHz.

In the high frequency limit, the dispersion relation predicts the sound speed with asymptote towards the sound speed of the pure vapor.

$$a_{mix}(\omega ==> \infty) = a_{fluid}$$

Interestingly, the high frequency limit is independent of both droplet size and liquid-to-vapor ratio.

Given the difficulties measuring sufficiently low frequencies to apply the quasi-steady model and recognizing that the high frequency sound speed contains no direct information on either droplet size or liquid-to-vapor ratio, it becomes apparent that the dispersive characteristics of the vapor/liquid mixture should be utilized to determine droplet size and liquid-to-vapor ratio based on speed of sound measurements.

As described hereinbefore, the probe 10 of the present invention includes the ability to accurately determine the average droplet size and the liquid/vapor ratio of the liquid in the vapor/liquid mixture. Provided there is no appreciable slip between the vapor and the liquid droplet, the propagation of one-dimensional sound wave through multiphase mixtures is influenced by the effective mass and the effective compressibility of the mixture. For an air transport system, the degree to which the no-slip assumption applies is a strong function of droplet size and frequency. In the limit of small droplets and low frequency, the no-slip assumption is valid. As the size of the droplet increases and the frequency of the sound waves increase, the non-slip assumption becomes increasing less valid. For a given average liquid droplet size, the increase in slip with frequency causes dispersion, or, in other words, the sound speed of the mixture to change with frequency. With appropriate calibration the dispersive characteristic of a mixture will provide a measurement of the average droplet size, as well as, the vapor to liquid ratio of the mixture.

Using the model described above, which yields the equation shown below, and experimentally determined sound speed as function of frequency, the present invention includes an optimization procedure to simultaneously determine droplet size and VLR in liquid/vapor mixtures:

$$a_{mix}(\omega) = a_f \sqrt{\frac{1}{1 + \frac{\varphi_p \rho_p}{\rho_f \left(1 + \omega^2 \frac{\rho_p^2 v_p^2}{K^2}\right)}}}$$

Referring to FIG. 11 there is shown an optimization procedure in accordance with the present invention in which the free parameters of an analytical model are optimized to minimize an error function. For illustration purposes, the error function utilized is the sum of the differences of the sound speeds between an analytical model and the experimentally determined sound speed as a function of frequency:

$$err = \sum_{f=f_{low}}^{f=f_{high}} (a(f)_{model} - a(f)_{measured})^2$$

Thus, the sound speed of a two-phase mixture varies with the ratio vapor and liquid phases present in the mixture. Through these relations, and using tabulated values for the sound speed and densities of the liquid and vapor phases of a process mixture, one can construct an explicit relationship between mixture sound speed and mixture quality. It should be noted that the Wood equation is an engineering approximation, the accuracy of which is dependent on the validity of a variety of assumptions. Experimental data may be required to define between quality and sound speed within required, but to be defined, accuracy limits. Various curves are produced in FIG. 12 showing the relationship of sound speed versus steam quality for well-mixed saturated steam mixtures over of range of temperatures and pressures.

As is known in the art, the relationship between quality of a vapor/liquid mixture, a mass ratio, and the volumetric phase fraction of the vapor phase is dependent on the properties of the vapor and liquid phases. For steam the relationship is shown in FIGS. 12 and 13. According to an empirical flow model, the assumption of well mixed, mist-like flows are typically applicable for process mixtures having vapor volumetric phase fractions greater than 0.83 and with mixture velocities exceeding 3.5*sqrt(D*g), where D is the tube 14 diameter and g is the acceleration due to gravity. For example, an 18 inch diameter steam tube translates to mixture velocities greater than ~8 m/s (~26 ft/sec).

Figure 14:
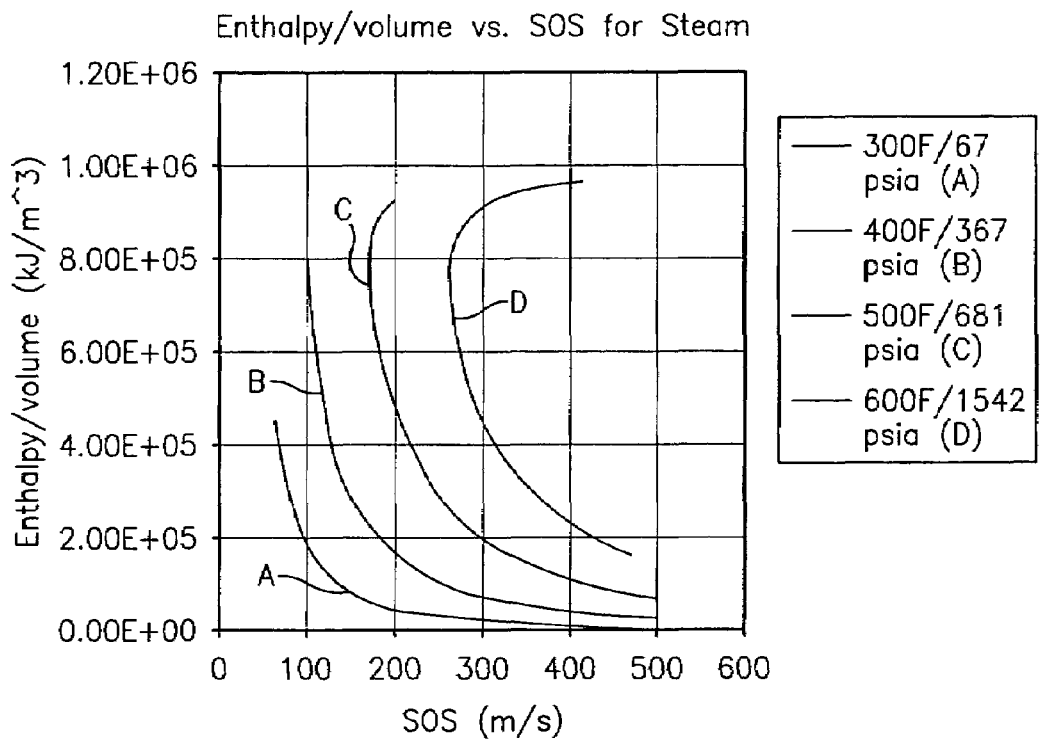
FIG. 14 is a plot of the enthalpy/volume for vapor/liquid mixtures having varying temperature and pressures versus the speed of sound propagating through the mixture, in accordance with the present invention.
Figure 15:
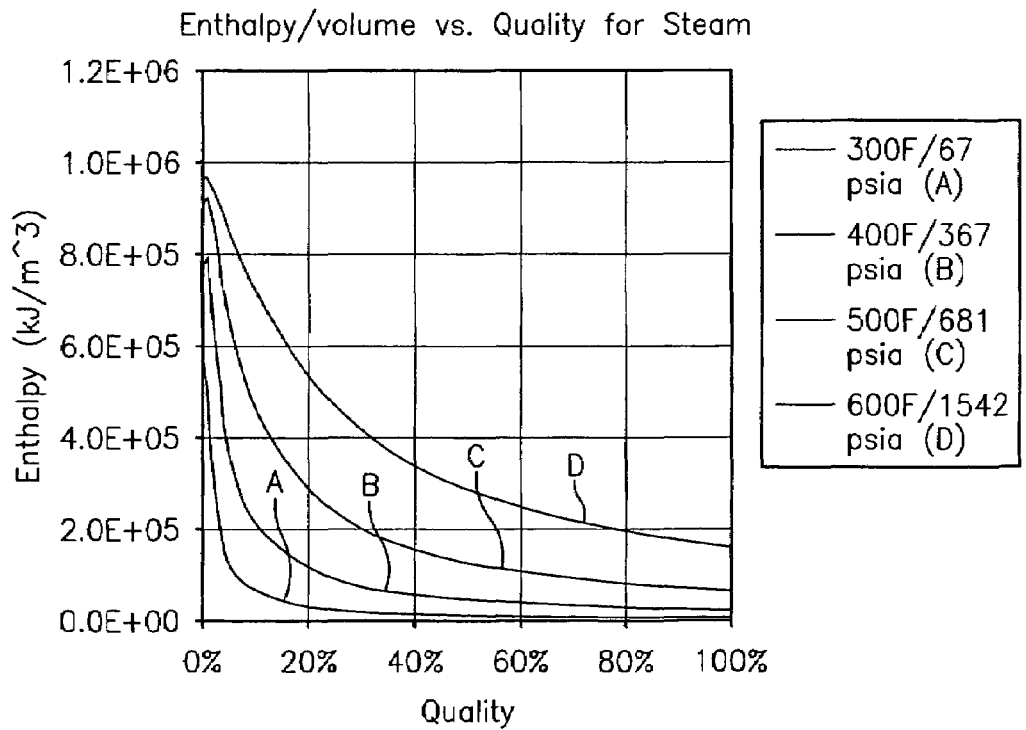
FIG. 15 is a plot of the enthalpy/volume for vapor/liquid mixtures having varying temperature and pressures versus quality of the mixture, in accordance with the present invention.
Figure 16:
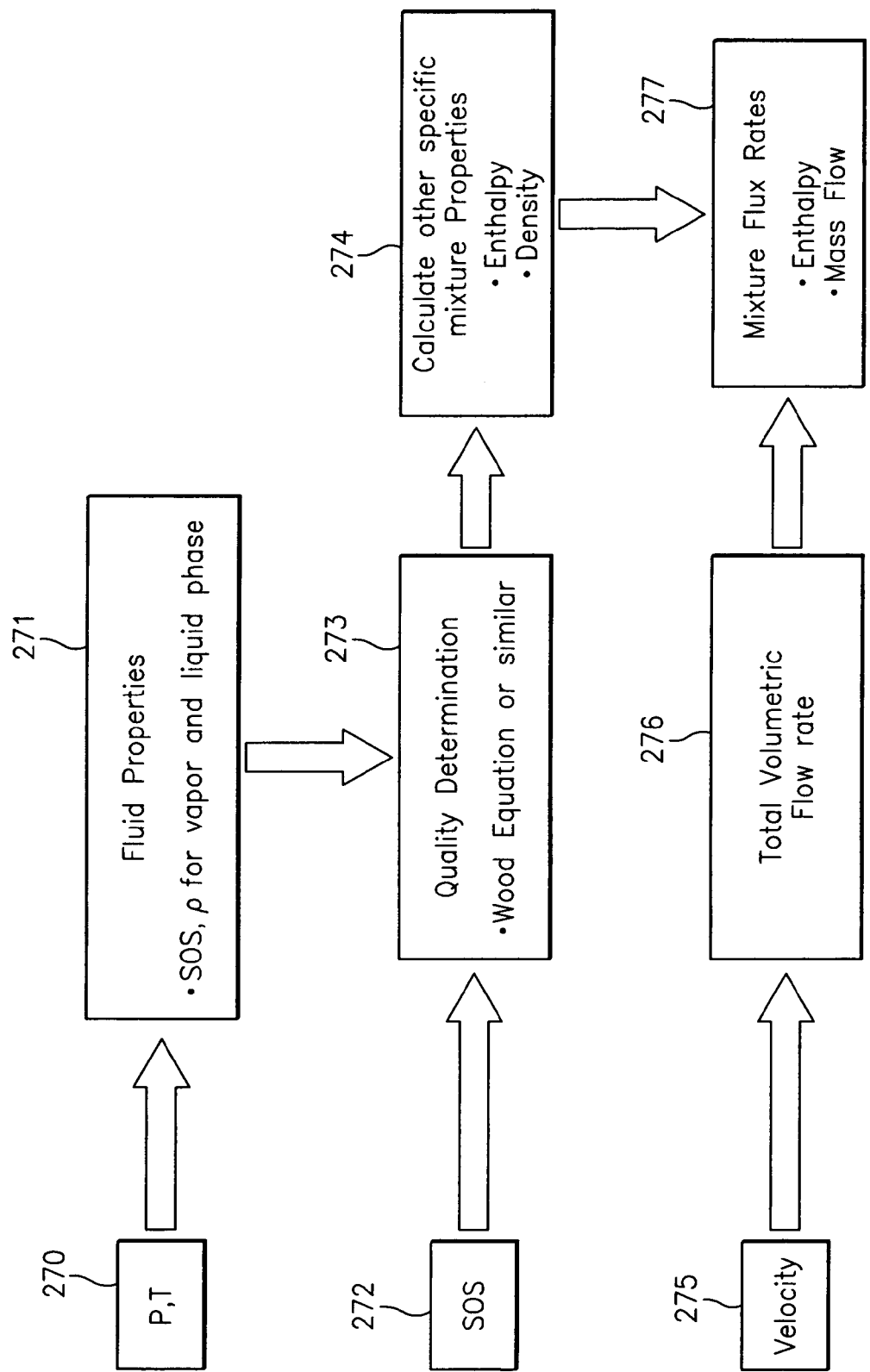
FIG. 16 is a schematic diagram of another embodiment of a probe embodying the present invention.

As developed above, determining the enthalpy flux of a steam mixture is an important measurement. In accordance with the present invention when the total volumetric flow of the mixture is known, the enthalpy per unit volume of the mixture is needed to determine the total flow rate. FIG. 14 shows the relationship between enthalpy per unit volume and mixture sound speed for steam at a variety of conditions. The present invention further utilizes the relationship between enthalpy per unit volume and mixture sound speed for steam at a variety of conditions and the relationship between enthalpy per unit volume and steam quality as shown in FIG. 15 to determine the quality of steam of a flow.

In addition to measuring the liquid to vapor ratio of the mixture 12 and droplet size of the liquid suspended in the mixture using the measured speed of sound, the probe 10 further includes the ability to measure of volumetric flow rate of the mixture by comparing the difference of the speed of an ultrasonic signal propagating with the mean flow and an ultrasonic signal propagating against the mean flow.

The interaction results in sound waves propagating with the mean flow traveling at the speed of sound (if the vapor/liquid mixture were not flowing) plus the convection velocity and, conversely, sound waves traveling against the mean flow propagating at the speed of sound minus the convection velocity as illustrated in FIG. 2. That is, $$a_R = a_{mix} + u$$

$$a_L = a_{mix} - u$$

where $a_R$=velocity of a right traveling ultrasonic signal relative to a stationary observer (i.e. the tube 14), $a_L$=velocity of a left traveling ultrasonic signal apparent to a stationary observer, $a_{mix}$=speed of sound traveling through the mixture (if the mixture was not flowing) and u=the mean flow velocity (assumed to be flowing from left to right in this instance). Combining these two equations yields an equation for the mean velocity, $$u = \frac{a_R - a_L}{2}$$

Therefore, by measuring the propagation velocity of ultrasonic signals in both directions relative to the stationary tube 14 as described hereinbefore, the mean flow velocity can be calculated by multiplying the mean flow velocity by the cross-sectional area of the tube 14.

The practicality of using this method to determine the mean flow is predicated on the ability to resolve the sound speed in both directions with sufficient accuracy to determine the volumetric flow. For typical vapor liquid measurements, flow velocities are typically at ~10 ft/sec and sound speeds of ~4000 ft/sec. Thus axial mach numbers are on the order of 10/4000 of 0.0025. For a +/−10% accuracy in flow rate (+/−1 ft/sec), the sound speed of the upstream and downstream propagating waves would need to be resolved to +/−0.5/4000 or 1 part in 8,000.

FIG. 17 illustrates another method of determining the transit time measurement know as the sing around method. As shown a series of ultrasonic transmitters and receivers propagate a series of ultra sonic signals wherein the receivers measure the transit time.

While a couple of methods have been described to measure transit time of an ultrasonic signal through a fluid, the present invention contemplates that any method of measuring the transit time of an ultrasonic signal may be used to determine the speed of sound of the fluid for determining parameters of the fluid.

However, for saturated vapor/liquid mixture flows, axial flow velocities are nominally around 70 ft/sec with no flow sound speeds of ~700 ft/sec. This results in mach numbers of ~0.1, approximately 2 orders of magnitude greater than typical vapor flows. For saturated vapor/liquid flows, to resolve the flow rate to 10% accuracy (or +/−7 ft/sec), one would have to resolve the sound speed to +/−3.5 ft/sec, or 3.5/700 or 1 part in 200.

While the apparatus 10 of FIGS. 2–7 has been described as a probe, the present invention contemplates that the apparatus may be use to measure fluid flow within a pipe, such as an industrial process pipe.

It should be understood that any of the features, characteristics, alternatives or modifications described regarding a particular embodiment herein may also be applied, used, or incorporated with any other embodiment described herein.

Although the invention has been described and illustrated with respect to exemplary embodiments thereof, the foregoing and various other additions and omissions may be made therein and thereto without departing from the spirit and scope of the present invention.

What is claimed is:

1. An apparatus for measuring the composition of a mixture flowing through a pipe, said apparatus comprising:
    an ultrasonic sensor apparatus disposed along the pipe that transmits an ultrasonic signal through the mixture and receives the ultrasonic signal, to provide a measured signal indicative of the transit time of the ultrasonic signal through the mixture, wherein the mixture includes particles suspended within a fluid; and
    a processor, responsive to said measured signal, that determines the speed of sound propagating through the mixture and, responsive to the speed of sound, that determines an output signal indicative of the composition of the mixture flowing through the pipe by determining the speed of sound propagating through the mixture as a function of frequency to characterize dispersion properties of the mixture and comparing the dispersion properties of the mixture to a dispersion model of the mixture.

2. The apparatus of claim 1, wherein the apparatus is a probe wherein the pipe comprises a tube having an open input end and open output end for receiving the mixture.

3. The apparatus of claim 1, wherein the wavelength of the ultrasonic signal is less than the length scale of the particles within the mixture.

4. The apparatus of claim 1, wherein the ultrasonic sensor apparatus includes at least three ultrasonic transducers disposed axially along the pipe to determine the transit time.

5. The apparatus of claim 1, wherein the wavelength of the ultrasonic signal is orders of magnitude greater than the length scale of the particles within the mixture.

6. The apparatus of claim 1, wherein the ultrasonic sensor apparatus comprises a first ultrasonic transducer disposed at an axial location along the pipe to transmit the ultrasonic signal into the mixture; and a second ultrasonic transducer disposed at an axial location along the pipe to receive the ultrasonic signal from the ultrasonic transducer.

7. The apparatus of claim 6, wherein the first ultrasonic transducer is axially spaced from the second ultrasonic transducer along the pipe.

8. The apparatus of claim 1, wherein the mixture is liquid droplets suspended in gas.

9. The apparatus of claim 1, wherein the mixture is solid particles suspend in a liquid or gas.

10. The apparatus of claim 1 wherein the dispersion model is empirically derived.

11. The apparatus of claim 1 wherein the dispersion model is numerically derived.

12. The apparatus of claim 1 wherein the composition of the mixture includes the phase fraction of the mixture.

13. The apparatus of claim 1 wherein the composition of the mixture includes the size of the particles.

14. An apparatus for measuring the composition of a mixture flowing through a pipe, said apparatus comprising:
an ultrasonic sensor apparatus disposed along the pipe that transmits an ultrasonic signal through the mixture and receives the ultrasonic signal, to provide a measured signal indicative of the transit time of the ultrasonic signal through the mixture, wherein the mixture includes particles suspended within a fluid; and
a processor, responsive to said measured signal, that determines the speed of sound propagating through the mixture and, responsive to the speed of sound, that determines an output signal indicative of the composition of the mixture flowing through the pipe using a dispersion model, wherein the dispersion model is:

$$a_{mix}(\omega) = a_f \sqrt{\frac{1}{1 + \frac{\varphi_p \rho_p}{\rho_f \left(1 + \omega^2 \frac{\rho_p^2 v_p^2}{K^2}\right)}}}$$

wherein $a_{mix}$ is the speed of sound propagating through the mixture, $a_f$ is the speed of sound propagating through the fluid, K is a proportionality constant, $\omega$ is frequency in rad/sec, $\phi_p$ is the volumetric phase fraction of the particles, $\rho_p$ is the density of the particles, $v_p$ is the volume of individual particles, and $\rho_f$ is the density of the fluid.

15. An apparatus for measuring the composition of a mixture flowing through a pipe, said apparatus comprising:
an ultrasonic sensor apparatus disposed along the pipe that transmits an ultrasonic signal through the mixture and receives the ultrasonic signal, to provide a measured signal indicative of the transit time of the ultrasonic signal through the mixture, wherein the mixture includes particles suspended within a fluid; and
a processor, responsive to said measured signal, that determines the speed of sound propagating through the mixture and, responsive to the speed of sound, that determines an output signal indicative of the composition of the mixture flowing trough the pipe using a dispersion model, wherein the processor compares at least a transitional frequency range of the dispersion model to determine the average size of the particles in the mixture.

16. An apparatus for measuring the composition of a mixture flowing trough a pipe, said apparatus comprising:
an ultrasonic sensor apparatus disposed along the pipe that transmits an ultrasonic signal through the mixture and receives the ultrasonic signal, to provide a measured signal indicative of the transit time of the ultrasonic signal through the mixture, wherein the mixture includes particles suspended within a fluid; and
a processor, responsive to said measured signal, that determines the speed of sound propagating through the mixture and, responsive to the speed of sound, that determines an output signal indicative of the composition of the mixture flowing through the pipe using a dispersion model, wherein the processor compares at least one of the lower frequency range and the transitional frequency range of the dispersion model to determine the phase fraction of the mixture.

17. A method for measuring the composition of a mixture in a pipe, said method comprising:
measuring the transit time of an ultrasonic signal propagating through the mixture, wherein the mixture includes particles suspended within a fluid; and
determining the composition of the mixture by determining the speed of sound propagating through the mixture as a function of frequency, in response to the measured transit time, to characterize dispersion properties of the mixture and comparing the dispersion properties of the mixture to a dispersion model of the mixture.

18. The method of claim 17, wherein the wavelength of the ultrasonic signal is less than the length scale of the particles within the mixture.

19. The method of claim 17, wherein the wavelength of the ultrasonic signal is orders of magnitude greater than the length scale of the particles within the mixture.

20. The method of claim 17, wherein the mixture is liquid droplets suspended in gas.

21. The method of claim 17, wherein the mixture is solid particles suspend in a liquid or gas.

22. The method of claim 17, wherein the dispersion model is empirically derived.

23. The method of claim 17, wherein the dispersion model is numerically derived.

24. The method of claim 17, wherein the composition of the mixture includes the phase fraction of the mixture.

25. The method of claim 17, wherein the composition of the mixture includes the size of the particles.

26. A method for measuring the composition of a mixture in a pipe, said method comprising:
measuring the transit time of an ultrasonic signal propagating through the mixture, wherein the mixture includes particles suspended within a fluid;
determining the composition of the mixture by determining the speed of sound propagating through the mixture in response to the measured transit time, and using a dispersion model, and
comparing at least a transitional frequency range of the dispersion model to determine the average size of the particles in the mixture.

27. A method for measuring the composition of a mixture in a pipe, said method comprising:
measuring the transit time of an ultrasonic signal propagating through the mixture, wherein the mixture includes particles suspended within a fluid;
determining the composition of the mixture by determining the speed of sound propagating through the mixture in response to the measured transit time, and using a dispersion model, and
comparing at least one of the lower frequency range and the transitional frequency range of the dispersion model to determine the phase fraction of the mixture.

* * * * *